US009795789B2

(12) United States Patent
Kaiser

(10) Patent No.: US 9,795,789 B2
(45) Date of Patent: Oct. 24, 2017

(54) SYSTEMS AND METHODS TO OPTIMIZE ANTI-TACHYCARDIAL PACING (ATP)

(71) Applicant: CardioFlow Technologies, LLC, Nashville, TN (US)

(72) Inventor: Daniel Walter Kaiser, Palo Alto, CA (US)

(73) Assignee: CARDIOFLOW TECHNOLOGIES, LLC, Nashville, TN (US)

( * ) Notice: Subject to any disclaimer, the term of this patent is extended or adjusted under 35 U.S.C. 154(b) by 0 days.

(21) Appl. No.: 14/811,719

(22) Filed: Jul. 28, 2015

(65) Prior Publication Data

US 2016/0030743 A1     Feb. 4, 2016

Related U.S. Application Data

(60) Provisional application No. 62/030,520, filed on Jul. 29, 2014.

(51) Int. Cl.
| | |
|---|---|
| *A61N 1/36* | (2006.01) |
| *A61N 1/362* | (2006.01) |
| *A61N 1/365* | (2006.01) |
| *A61B 5/00* | (2006.01) |
| *A61B 5/0464* | (2006.01) |

(52) U.S. Cl.
CPC ....... *A61N 1/3622* (2013.01); *A61N 1/36514* (2013.01); *A61B 5/0464* (2013.01); *A61B 5/7282* (2013.01)

(58) Field of Classification Search
CPC .. A61N 1/3622; A61N 5/0464; A61N 1/3624; A61B 5/7282
USPC .......................................................... 607/14
See application file for complete search history.

(56) References Cited

U.S. PATENT DOCUMENTS 6,766,196 B1    7/2004   Kroll et al.
2011/0319952 A1* 12/2011   Virag ..................... A61B 5/046
                                                          607/14

FOREIGN PATENT DOCUMENTS

EP           2004284 B1    11/2011

OTHER PUBLICATIONS

Korean Intellectual Property Office, PCT International Search Report for PCT/US2015/042536, Applicant: Cardioflow Technologies, LLC, Form PCT/ISA/220; dated Nov. 26, 2015, 5 pages.

(Continued)

*Primary Examiner* — Paula J Stice
(74) *Attorney, Agent, or Firm* — William A. English; Vista IP Law Group LLP

(57) ABSTRACT

Apparatus, systems and methods are provided for prevention and/or remediation of cardiac arrhythmias, e.g. optimizing anti-tachycardia pacing (ATP) algorithms. More particularly, implantable devices are provided that measure and treat cardiac arrhythmias. By monitoring the ATP attempt from additional electrodes, far-field morphology analyses, and/or measuring the return interval from a failed ATP attempt; the devices may estimate when entrainment has occurred, the amount of delay within the reentrant tachycardia, and/or tachycardia termination/acceleration. These variables and occurrences can be used to optimize the first and/or subsequent ATP attempts. Furthermore, other exemplary embodiments describe methods to integrate electrical restitution properties into the design of ATP pacing algorithms to facilitate tachycardia termination.

18 Claims, 11 Drawing Sheets

(56) References Cited

OTHER PUBLICATIONS

Korean Intellectual Property Office, PCT Written Opinion for PCT/US2015/042536, Applicant: Cardioflow Technologies, LLC, Form PCT/ISA/237; dated Nov. 26, 2015, 7 pages.

* cited by examiner

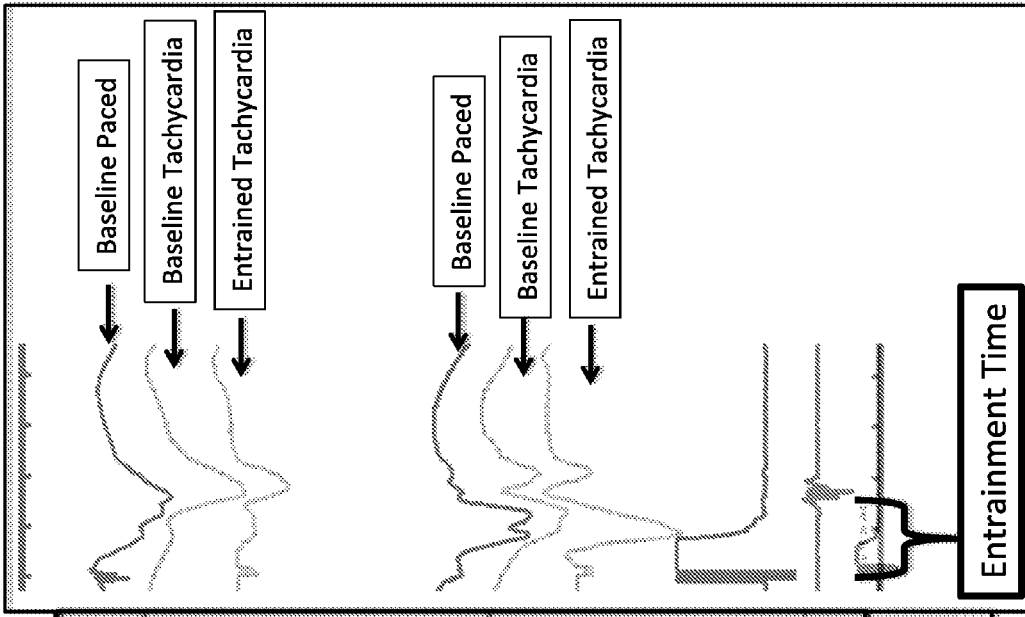
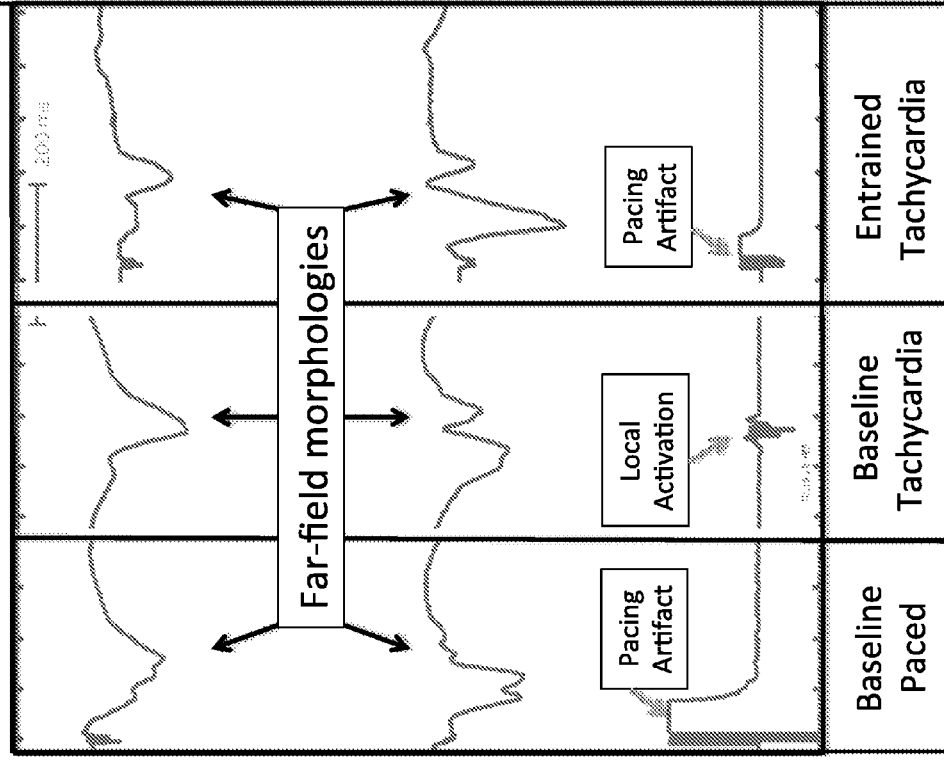

SYSTEMS AND METHODS TO OPTIMIZE ANTI-TACHYCARDIAL PACING (ATP)

RELATED APPLICATION DATA

This application claims benefit of provisional application Ser. No. 62/030,520, filed Jul. 29, 2014, the entire disclosure of which is expressly incorporated by reference herein.

FIELD OF THE INVENTION

This invention is in the field of devices and methods to diagnose and treat cardiac arrhythmias.

BACKGROUND

Abnormally fast heart rates are called tachycardias. When the tachycardia occurs in the top chambers of the heart (the atria), this is termed atrial tachycardia. When it occurs in the bottom chambers (the ventricles), this is termed ventricular tachycardia. These rhythms can be highly symptomatic in the case of atrial tachycardia or can be life-threatening in the case of ventricular tachycardia.

These rhythms are often due to diseased or dead myocardial tissue, which may form a scar. Under normal conditions, all myocardial cells conduct electrical activity. When a myocardial cell depolarizes, the ionic membrane potential changes; which as a result, can cause its neighbor myocardial cell to depolarize, and so on. Therefore, depolarizing cells result in a self-propagating mechanism, whereby depolarizing wavefronts travel through myocardial tissue. In certain settings, a propagating wavefront may travel around non-conducting tissue. If each cell along this reentrant pathway has enough time to repolarize the cell's membrane potential, the resulting wavefront can then get caught in a perpetual loop where the electrical signal in the myocardial tissue circles around a fixed point or central scar. The action potentials will continually propagate around the non-conducting tissue (such as a prior myocardial infarction) at a rate considerably faster than the heart's intrinsic rate. The reentrant circuit can be thought of as a conduction wavefront propagating along a tissue mass of approximately circular geometry.

Initially, these dangerous rhythms were treated with an external shock (defibrillation) that resets the myocardial tissue to regain normal sinus rhythm. As implanted devices became more complex, pacing modalities were created to attempt to pace-terminate the tachycardia. This is termed anti-tachycardia pacing (ATP). When ATP strategies fail, the device may then proceed with painful how powered shocks; which usually are very painful to the patient. ATP, on the other hand, is usually painless.

The rate at which myocardial tissue can allow a propagating wavefront to conduct through it has a limit. Once depolarized, the tissue must repolarize in order to conduct another propagating wavefront. If a wavefront approaches myocardial tissue which has not repolarized the tissue cannot conduct the wavefront and the electrical signal will terminate. Tissue that has not yet repolarized and cannot conduct an electrical signal is termed refractory.

To terminate an arrhythmic circuit, a pacing stimulus is provided at a time and location such that the resulting wave propagation fails to conduct down the pathway of the reentrant circuit. When pacing faster than the reentry tachycardia, the paced stimulation wavefront proceeds toward the arrhythmic circuit. This wavefront can approach both sides of the reentrant circuit (see FIG. 4 for clarity); such that the wavefront will collide with the wavefront leaving the reentrant circuit (termed the 'exit' site). With more pacing, the paced wavefront will reach the native tachycardia prior to the reentrant wavefront; resulting in an earlier depolarization of the reentrant circuit. With substantially continuous pacing, we can reach "entrainment," whereby the wavefront traveling towards the exit site, will collide with the wavefront from the prior wavefront within the arrhythmic circuit (in the retrograde direction). The paced wavefront will also proceed towards the entrance site of the reentrant tachycardia and proceed down the path of the arrhythmic circuit in the orthograde direction. If the pacing rate is accelerated, this orthodromic wavefront may reach a part of the arrhythmia circuit before it has repolarized and is therefore refractory. If this occurs, the wavefront may terminate and the arrhythmia will end. Accordingly, the probability of anti-tachycardia pacing (ATP) succeeding in terminating a tachycardia is related to the ability of the pacing stimulation wavefront to arrive at the location of the reentrant circuit in such a manner that the propagating signal in the reentrant circuit is modified, is unable to perpetuate the propagating signal, and the tachycardia is terminated.

Numerous different pacing modalities and algorithms have been created for the termination of tachycardia. These algorithms have been created for both atrial and ventricular tachycardias. These algorithms are programmed into implanted devices such as a pacemaker or implantable cardioverter-defibrillators (ICDs). These devices may deliver a high powered electrical shock which attempts to reset all cells involved in the reentrant tachycardia in order to terminate the tachycardia. These shocks are often painful and can cause harm to myocardial cells. Alternatively, the devices may deliver anti-tachycardia pacing (ATP), whereby paced wavefronts reach critical aspects of the reentrant circuit in such a manner that the tachycardia terminates. ATP is usually painless and therefore has advantages over high-powered cardioversions.

ATP is not always successful at terminating the tachycardia. In this circumstance, the ATP is repeated at the same or different pacing algorithm in attempts to terminate the arrhythmic into a normal sinus rhythm. If ATP is unsuccessful, the patient may require high voltage cardioversion. ATP is unsuccessful in approximately 10-40% of ATP attempts. In addition, ATP sometimes accelerates the rhythm to a faster rate or may degenerate the rhythm into ventricular fibrillation, which is a chaotic rhythm that is not capable of sustaining life. Furthermore, the longer the patient is in ventricular tachycardia, the more likely the patient is to pass out (syncope) which is dangerous.

Thus, improved methods for increasing the success rate of ATP and for decreasing the time in tachyarrhythmia, which will reduce the need for painful ICD shocks, are needed.

ATP often functions by entraining the tachycardia. Entraining is a process whereby paced beats (by a pacemaker lead, for example) accelerates the tachycardia. One or more stimulations are provided at a rate slightly faster than the tachycardia, such that the paced wavefronts enter and accelerate the tachycardia. The first paced stimulation that advances the reentrant tachycardia resets the tachycardia. The next pacing stimulation typically advances the tachycardia to the paced cycle length. Since myocardial tissue properties often change in response to shorter cycle lengths, several resetting stimulations may be needed to completely advance the tachycardia to the pacing cycle length. Each paced beat then 'resets' the tachycardia to the faster rate, termed entrainment. Ideally, the faster rate is too fast for the arrhythmic circuit, such that the tissue has not had enough time to repolarize. In this case, the wavefront terminates, and the patient returns to sinus rhythm.

Entrainment involves identifying a specific response of a reentrant arrhythmia to external pacing, including: (1) beat to beat interaction between the paced and tachycardia wavefront; (2) activation of all the tissue in the chamber where the circuit is located; and (3) persistence of the tachycardia after pacing, if the tachyarrhythmia does not self-terminate. If the self-sustaining tachyarrhythmia of the heart is thought of as an electrical circuit running in a circle, one can "entrain" that circuit by pacing slightly faster than the circuit was running on its own. This is known as resetting the circuit, as the tissue in the circuit will now be excited at the new, faster, paced rate, as compared to the pace at which the circuit ran on its own before entrainment. If the circuit can propagate at the faster rate, when this re-setting is stopped, the pacing catheter electrode in the heart can then measure the time required for the last paced beat to create a wavefront, enter the arrhythmic circuit, propagate around a portion of the arrhythmic circuit, and then exit to the same electrode or catheter. This time is termed the post-pacing interval (PPI). The post-pacing interval has long been used as an indication of the proximity of the pacing site to the reentry circuit. (Stevenson, Khan et al. 1993) (Waldo 1997).

The efficacy of the delivery of anti-tachycardia pacing (ATP) through the right ventricular implantable cardioverter defibrillator (ICD) lead to terminate life-threatening fast ventricular tachycardia (FVT) was first published in 2001 by Wathen et al. In this study, the authors revealed that ATP could prevent ICD shock delivery in 3 of 4 episodes. Over the following years, ATP has become a valuable option to treat most VT episodes. Large-scale studies, including Pain-Free Rx II, EMPIRIC, PREPARE, or ATPonFastVT, have demonstrated the efficacy and safety of this approach. Moreover, delivering ATP instead of defibrillation has dramatically reduced the number of painful ICD shocks.

Typically, the ATP algorithm depends on the type (atrial versus ventricular) and rate of the tachycardia. For example, most device makers make a distinction between ventricular tachycardia (VT), fast ventricular tachycardia (FVT), and ventricular fibrillation (VF) based on the rate of the tachycardia. The tachycardia rate can be described in terms of beats per minute (BPM) or can be thought of as the time between heart beats (termed the RR interval). This time is also termed the tachycardia cycle length (TCL), and is often given in milliseconds, 60,000 divided by the heart rate provides the cycle length in milliseconds (ms). For example, a tachycardia of 200 BPM has a tachycardia cycle length of 300 ms.

ATP can be a pacing train of a certain cycle length (burst pacing) or can shorten the cycle length with each additional paced beat (often termed ramp pacing). Ramp therapy consists of a decremental drive of a programmable number of pulses, starting at a rate proportional to the current tachycardial cycle length (TCL).

The current algorithms of ATP are well known and easily accessible. One example (described below) is by implantable device maker Medtronic, although all device makers have created similar pacing algorithms.

In Medtronic's PainFREE Rx II Trial, the first therapy in the FVT zone (188-250 BPM) was 2 ATP sequences (8-pulse burst pacing train at 88% of the FVT cycle length). If the first ATP sequence was unsuccessful, the second sequence was delivered at 88% of the FVT cycle length minus 10 ms. ATP therapies were delivered at maximum voltage and pulse duration. Programming of subsequent FVT therapies was left to the investigators' discretion and usually involved ICD shocks.

A recent study by Martins et al published in Eurospace (2012) performed a study involving the major ICD device makers: Biotronik, Boston Scientific, Medtronic, St Jude Medical and Sorin Group companies. In this study, the ventricular ATP algorithm was as follows: Implantable cardioverter/defibrillators were programmed to deliver 10 ATP attempts for FVT cycle lengths (CLs) of 250-300 ms (200-240 BPM) before shock delivery (5 bursts, then 5 ramps; 8-10 extrastimuli at 81-88% FVT CL; minimal pacing CL 180 ms). A total of 1839 FVTs, 1713 of which were ATP-terminated (unadjusted efficacy ¼ 93.1%, adjusted ¼ 81.7%). Furthermore, over 20% of the patient experienced. ATP that required more than two episodes of ATP.

Thus, there is room to improve the current ATP algorithms to reduce the time spent in tachycardia and prevent ICD shock.

The most advanced pacemakers feature atrial preventive pacing and atrial anti-tachycardia pacing (DDDRP), which may reduce atrial fibrillation occurrence and duration. The device automatically delivers ATP therapies when an episode is classified as atrial tachycardia and lasts longer than a programmable 'time to first therapy' (often 1 min). Often, ramp is programmed in order to deliver three series of ten sequences each, so that each patient could receive up to thirty termination attempts. Each series begins with a train of ten pulses. The first pulse of each of the three series is delivered at 91, 84, and 81% of the underlying atrial tachycardia cycle length (ATCL), respectively. In each series, subsequent pulses were delivered with a decrement in pacing coupling interval of 10 ms each. If a previous train fails to terminate AT, an additional stimulus is added to the next train.

Burst+ therapy uses a drive of a programmable number of atrial pulses, the rate of which is proportional to the current ATCL, followed by up to two extrastimuli. Burst+ is programmed in order to deliver three series of ten sequences each; each sequence is made up of fifteen pulses followed by two extrastimuli. As in the Ramp programming, each patient can receive up to thirty termination attempts. The first scan of each series is released at 84% of the underlying ATCL. The first extrastimulus is delivered at 81% of the underlying ATCL; the second extrastimulus was delivered with an interval reduced by 20 ms. In the event of failure, the ATP train coupling interval was decreased by 10 ms for each subsequent scan.

For both therapies, the minimal pacing interval (MPI) was 150 ms, so that pulses programmed at a shorter pacing interval than the MPI were delivered at the MPI value. Atrial ATP was recently found to significantly reduce the progression of atrial tachycardia to permanent atrial fibrillation (61% relative risk reduction) over a 2 year follow-up.

Previous methods use similar strategies for all tachycardias. These strategies use a burst or a ramp strategy with variable number of beats. If this ATP attempt fails, another burst or ramp is delivered at shorter intervals (faster rates). We have devised unique pacing algorithms based on novel concepts to improve the ability of a device to terminate a tachycardia.

SUMMARY

The present invention is directed to apparatus, systems and methods for prevention and/or remediation of cardiac arrhythmias, e.g. optimizing anti-tachycardia pacing (ATP)

algorithms. More particularly, the present invention is directed to implantable devices that measure and treat cardiac arrhythmias. By monitoring the ATP attempt from additional electrodes, far-field morphology analyses, and/or measuring the return interval from a failed ATP attempt; the present application describes examples where the device estimates the timing of entrainment, the amount of delay within the reentrant tachycardia, and/or tachycardia termination/acceleration. These variables and occurrences can be used to optimize the first and/or subsequent ATP attempts. Furthermore, other exemplary embodiments describe methods to integrate electrical restitution properties into the design of ATP pacing algorithms to facilitate tachycardia termination.

In one exemplary embodiment, the device may identify reentrant tachycardias based on timing intervals, far-field morphology, and/or the time differences between multiple electrodes. The device may also monitor for arrhythmia entrainment and/or termination during deliver of ATP to optimize the current and future ATP algorithms. By measuring dynamic responses occurring from overdrive pacing from far-field morphology and/or timing intervals of cardiac signals from additional electrode(s), other embodiments herein may estimate and record certain aspects of the ATP attempt, such as the total premature pacing time required to entrain the tachycardia ("the Time to Entrainment"), conduction delay occurring within the tachycardia circuit (the "Time Delay"), changes in the tachycardia (such as tachycardia acceleration), tachycardia termination, and the prior successfulness and failures of certain ATP strategies. As is described in the following text and figures, the device can use these measurements and occurrences to improve the probability of tachycardia termination by leveraging electrical restitution properties of myocardial tissue. Examples are described herein of organizing the initial pacing intervals to minimize partial tachycardia acceleration as well as the strategy of delivering "priming" pacing pulses, or pulses delivered at longer intervals than typically seen in anti-tachycardia pacing attempts; in efforts to slow repolarization rates in critical aspects of the arrhythmic circuit. These methods will therefore improve the successfulness of ATP attempts, decrease the time the patient spends in dangerous tachyarrhythmias, and reduce the need for ICD shocks. Therefore, the following concepts are advantageous to programming and designing device ATP capabilities and algorithms.

Other aspects and features of the present invention will become apparent from consideration of the following description taken in conjunction with the accompanying drawings.

BRIEF DESCRIPTION OF THE DRAWINGS

In general, examples disclosed herein are directed to treating tachyarrhythmias, such as ventricular tachycardia, by employing at least one electrode to deliver electrical stimulation to a patient's heart in a manner designed to terminate a tachyarrhythmia episode.

FIGS. 4A and 4B reveal an example of intracardiac and far-field morphologies which illustrate how far-field morphology analyses can be utilized to estimate the Time to Entrainment.

DETAILED DESCRIPTION OF THE EXEMPLARY EMBODIMENTS

Figure 1:
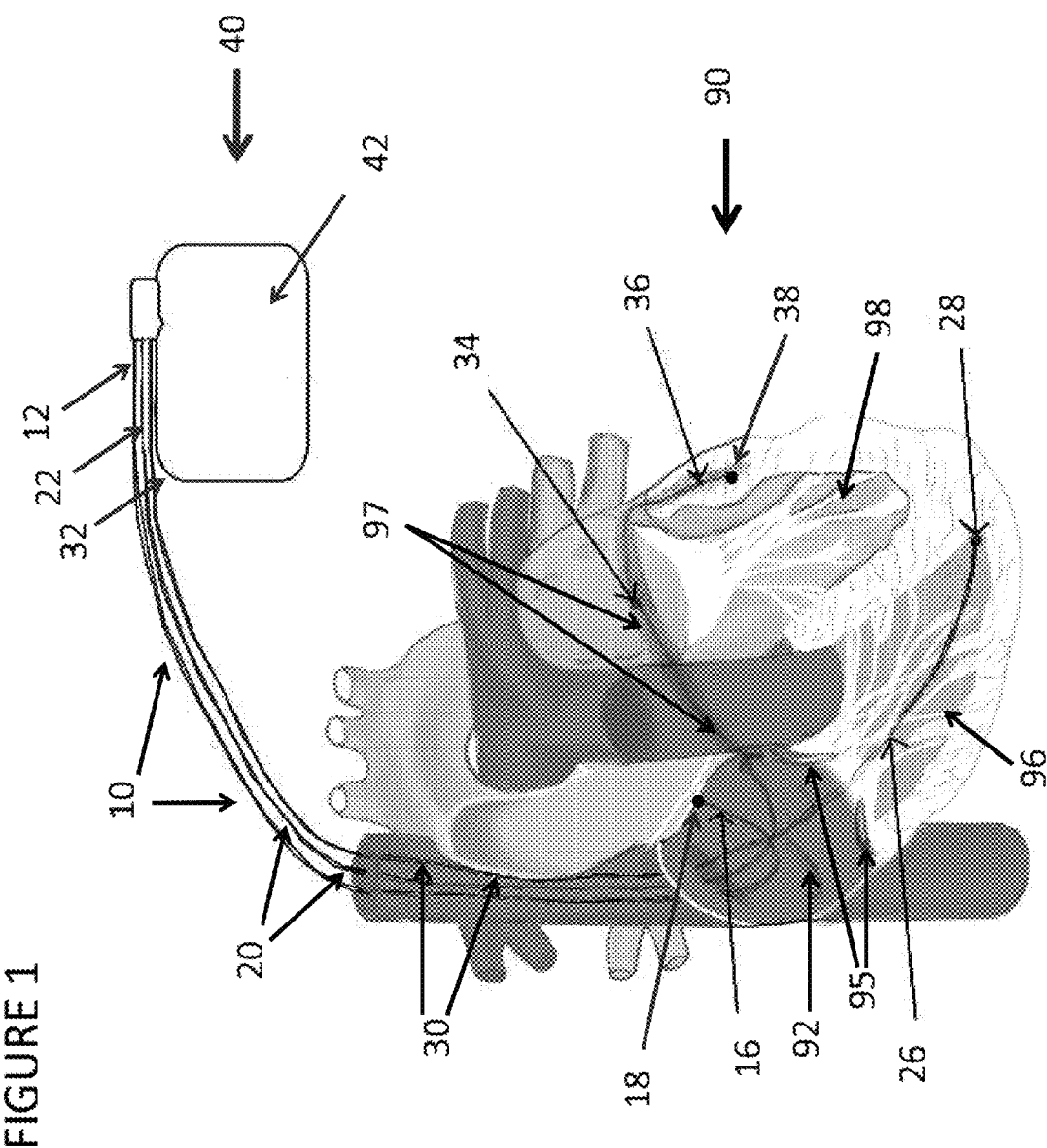
FIG. 1 reveals a schematic diagram of a pacemaker/implantable cardio-defibrillator (ICD) with specialized leads going into the heart in which the present invention may be usefully practiced.

Overdrive pacing is typically performed at a rate faster than the native tachycardia; therefore the paced cycle length is usually shorter than the tachycardia cycle length (PCL<TCL). Each paced stimulation 'gains' on the native tachycardia by the amount of pacing prematurity, or the difference between the tachycardia cycle length and overdrive pacing cycle length (TCL−PCL). Overdrive pacing continues to 'gain' on the native tachycardia until the paced wave front reaches and then accelerates the native tachycardia. Once overdrive pacing reaches the arrhythmic circuit, additional pacing stimulations continuously resets the native tachycardia to the PCL (entrainment). Therefore, the total amount of time overdrive pacing "gains" on the native tachycardia before pacing begins to accelerate/reset the native tachycardia can be calculated in equation 1 based on the number of pacing simulations required to accelerate the tachycardia (n), the difference between the tachycardia cycle length and the paced cycle length (TCL-PCL) [which can be variable], minus the amount of tachycardia acceleration.

$$\text{Time Gained} = \sum_{0}^{n}(TCL - PCL) - \text{tachycardia advancement} \quad (1)$$

A distant electrode may be able to monitor the TCL, during overdrive pacing and estimate the timing of tachycardia entrainment and conduction delay within the reentrant tachycardia. The total amount of time overdrive pacing needs to gain on the native tachycardia in order to entrain the tachycardia can be approximated by the post-pacing interval minus the tachycardia cycle length (PPI−TCL). The post-pacing interval (PPI) or the return interval (RI) is the return interval that occurs after an entrainment maneuver or a failed ATP attempt. This time is the time required for the paced signal to travel from the pacing location, around the reentrant circuit, and then back to the pacing electrode. The faster the overdrive pacing cycle length, or the faster the anti-tachycardia pacing cycle length, the return cycle will prolong due to conduction velocity slowing; primarily in the reentrant circuit.

The total amount of time overdrive pacing must overcome in order to attain entrainment can be mathematically determined. The return cycle of the compensatory pause is equal to the TCL plus the amount of pacing prematurity (TCL−PCL). With additional pacing stimulations, the return cycle of the compensatory pause continues to prolong with each paced stimulation (equation 2). Once pacing reaches the arrhythmic circuit, the paced wavefront accelerates the native tachycardia, and the return cycle is shorter than would be predicted from a compensatory pause. Assuming minimal changes in conduction velocity, the return cycle of the first entrained beat, as well as all additional pacing stimulations, will be fixed at the PPI. In reality, there can be significant prolongations in the post-pacing interval secondary to changes in conduction velocity at a shorter cycle length. Generally, the uncorrected PPI can be determined by adding the tachycardia cycle length to the total amount of pacing prematurity, minus the amount of tachycardia advancement (equation 3).

Compensatory Pause $$\text{Return interval} = TCL + \text{stim number}(n)*(TCL-PCL) \quad (2)$$

At Entrainment $$PPI = TCL + n*(TCL-PCL) - \text{tachycardia advacement} \quad (3)$$

As can be seen, by re-arranging equation 3, the total amount of time gained by overdrive pacing must be equal to the PPI−TCL, which is also equal to the entrainment time, as can be seen in Equation 4.

$$PPI - TCL = n*(TCL - PCL) - \text{tachycardia advancement} = \text{Entrainment Time} \quad (4)$$

Finally, after adjusting for the slowing that occurs associated with the faster overdrive pacing (discussed in detail later), we can determine the corrected PPI, or PPIc; as well as the amount of conduction delay (time delay). By knowing this measurement, we can determine the number of pacing stimulations required to reach and accelerate the tachycardia at any cycle length, as shown in equation 5.

$$\frac{PPI_C - TCL}{TCL - PCL} = \text{number of pacing stimulations } (n) \quad (5)$$
$$\text{required to advance a tachycardia at any given } PCL$$

The following pacing stimulation will entrain the tachycardia to the PCL. When the tachycardia has been entrained, all electrodes within the pacing chamber (whether the atria or ventricles) will accelerate to the paced cycle length. Therefore, by having an electrode in the myocardial tissue receiving the depolarized wavefront exiting the reentrant tachycardia, the timing of entrainment can be estimated. Furthermore, the amount of delay within the reentrant circuit can be estimated with this electrode. In some circumstances, the time to entrainment can be difficult to estimate, even with optimal locations of the distal electrodes. This error can occur because the first stimulation accelerating the native tachycardia can introduce significant conduction delay, which may not be fully appreciated. Therefore, in some circumstances, overdrive pacing from more than one location can be performed. In this scenario, the entrainment time for electrode B can be determined by equation 6, where the time differences between the electrodes during entrainment at more than one location are utilized to estimate the entrainment time for electrode B. This equation assumes the overdrive pacing cycle length is similar for all entrainments.

$$\text{Entrain Time } B = \text{Stim}_{A \to B} + \text{Stim}_{B \to A} - PPI_{A \to A} \quad (6)$$

The PPI−TCL is equal to the sum of the pacing prematurity until entrainment is obtained. Furthermore, the PPI−TCL is also equal to the time difference between the pacing electrode and a distal electrode between an entrained tachycardia and the reentrant tachycardia. A similar method, which relies upon the post entrained stimulation (as opposed to the baseline interval) has been described by Stevenson as the N+1 rule (Friedman, 2001). Furthermore, because conduction tissue may slow with shorter cycle lengths or persistent pacing, the amount of conduction delay can be estimated by the time difference between the first entrained stimulation and a stable conduction time with persistent pacing. The prolongation in this time from persistent pacing or shorter cycle lengths can be used to estimate the conduction delay within the reentrant circuit.

Additionally, far-field waveform morphology analyses can help determine when a tachycardia has been entrained and the amount of conduction delay within the reentrant circuit. This is because during entrainment, the far-field morphology is the fusion between the paced morphology and the reentrant morphology. The differences between the far-field paced morphology, baseline reentrant morphology, and the fusion morphology can be used to estimate the timing of entrainment and the amount of delay within the reentrant circuit. With persistent pacing at a cycle length shorter than the tachycardia cycle length, there is progressive fusion between the paced waveform and the tachycardia waveform. When overdrive pacing results in a stable far-field morphology that is distinct with the far-field morphology that occurs with pacing from the pacing location, this finding identifies the tachycardia as entrained. Similar to a distal electrode analysis, the prematurity from each overdrive pacing pulse is aggregate until they sum to the entrainment time; at which point the pacing pulses accelerate the native tachycardia. The prematurity can be summed until the steady fusion morphology is obtained. Furthermore, by comparing the morphology between the far-field paced morphology at baseline, the baseline tachycardia morphology, and the fusion morphology of an entrained (and stable) tachycardia from the pacing electrode, the entrainment time can be estimated. Furthermore, if the morphology significantly changes to match the baseline paced morphology; this provides evidence of tachycardia termination. Furthermore, by comparing the Entrainment time and fusion morphology over a series of pacing stimulation, the Time delay occurring within the tachycardia circuit can be estimated. These variables can be combined to determine the optimal initial pacing algorithm to minimize partial acceleration; in addition, these variables can be used to optimize the "priming" pulse, to facilitate tachycardia termination.

The difference in time between the electrodes during the reentrant tachycardia can be used to estimate the time to entrainment. This is because the entrainment pathway may involve certain aspects of the tachycardia reentrant tachycardia. Since the conduction times between the electrodes can be measured prior to any tachycardia, the prematurity required to reset/entrain the tachycardia can be estimated. Therefore, in some circumstances (such as a very fast tachycardia), only one ATP attempt can be delivered prior to proceeding with cardiac defibrillation. In these circumstances, the time differences between electrodes can be combined with the conduction times when not in tachycardia can be used to deliver a single ATP attempt with an increased probability of minimizing tachycardia partial acceleration.

Additionally, when entraining a tachycardia, the pacing electrode(s) may be far from the entrain site into areas of slow conduction. When the entrance site is far away from the pacing location(s), overdrive pacing may advance much of the myocardium prior to advancing the entrance site. In these circumstances, the sensing electrodes and far-field pacing morphology may not be helpful in identifying conduction slowing within critical aspects of the reentrant circuit. Therefore, in yet another embodiment, the pacing electrode is selected using the time intervals between electrodes during the tachycardia. In general, the latest occurring electrode can be chosen. However, baseline conduction times and far-field morphology can be measured and compared against tachycardia time intervals and far-field morphology to determine the optimal pacing electrode from which to pace. In yet another embodiment, ATP pulses can be delivered from both electrodes, and based on the far-field morphology (or additional non-pacing electrode) the electrode closest to the entrance site can be used for subsequent pacing stimulations.

Therefore, the timing of tachycardia entrainment and the amount of delay within the reentrant circuit can be estimated by 1) measuring post-pacing interval to failed ATP attempts 2) by analyzing the timing of intracardiac signals from a distal electrode within the chambers of interest, and/or 3) by far-field morphology analyses. Knowing this can be used to optimize the first and subsequent ATP attempts.

Once the entrainment time and conduction delay is determined at a certain catheter location, the timing of tachycardia acceleration (and entrainment) can be determined at any overdrive pacing cycle length. Our studies have revealed that after adjusting for decremental conduction, the timing of entrainment can be estimated within a few milliseconds. Therefore, the entrainment time from the first or prior failed ATP attempt can be used to optimize subsequent ATP attempts. By knowing exactly when overdrive pacing will entrain the native tachycardia, the number of pacing stimulations can be limited in order to minimize the possibility of tachycardia acceleration or fibrillation. Additional pacing stimulations (after the tachycardia has been entrained and with stable conduction times) delay termination to the tachycardia, waste battery life, and significantly increase the risk of developing faster tachycardias and/or disintegration into fibrillation.

Secondly (and of much more clinical importance), electrical restitution properties change with overdrive pacing. The first pacing stimulation that reaches the arrhythmic circuit will accelerate the native tachycardia by some fraction of time between the TCL and the PCL; which is dependent upon many factors, including the distance between the pacing stimulation location and the reentrant tachycardia. If the first stimulation that reaches the arrhythmic circuit only partially accelerates the tachycardia to the PCL, the electrical restitution curves dictate the critical aspects of the reentrant circuit are more likely to tolerate the tachycardia when accelerated to the PCL. The relationship between depolarization rates and repolarization times is known as the electrical restitution curve. Therefore, partial acceleration may prepare the tachycardia to tolerate the ATP at faster overdrive pacing cycle lengths. The ATP algorithm can be set up such that the first pacing stimulation to accelerate the native tachycardia completely accelerates the tachycardia to the PCL (or desired interval). Delivering premature stimulations that only partially accelerate the native circuit may accelerate repolarization rates and make the tachycardia more difficult to pace-terminate. Furthermore, by monitoring the tachycardia in terms of tachycardia changes (such as tachycardia acceleration) or tachycardia termination; an ATP attempt can deliver stimulations and measure the response. If the accelerating pulses do not terminate the tachycardia, the device can deliver one or more stimulation(s) at a longer cycle length (for example, based upon the tachycardia cycle length) followed by a paced cycle length at an even shorter cycle length. Again, the tachycardia can be monitored for changes or termination. Therefore, the device can continue pacing and adjusting the pulsing cycle length in order to facilitate tachycardia termination without stopping the ATP attempt. By delivering pulses near the tachycardia cycle length, electrical restitution properties are leveraged to optimize tachycardia termination.

Current strategies of ATP can be improved by determining the exact time of tachycardia acceleration from overdrive pacing. The first beat to reach the reentrant circuit will accelerate the native tachycardia. However, the amount of time the first beat accelerates the native tachycardia will affect the ability of the ATP attempt to terminate the tachycardia. This is because the rate of cellular repolarization (the refractory period to the reentrant circuit) depends on the rate of depolarization. If the first stimulated wavefront to accelerate the tachycardia accelerates the native tachycardia by less than the difference between the tachycardia cycle length (TCL) and the overdrive pacing cycle length (PCL); the partially accelerated tachycardia will prepare the tachycardia to tolerate the overdrive pacing cycle length (PCL). Therefore, by determining the amount of time required in order to accelerate a tachycardia; the algorithm of overdrive pacing can be optimized to increase the successfulness of the ATP attempt. While conduction velocities may slow at shorter pacing cycle lengths and therefore serve to 'protect' al aspects of the reentrant circuit; repolarization rates tend to be more sensitive than conduction velocities in response to shortening diastolic intervals. That is to say, premature stimulations rarely prolong conduction times across the critical isthmus, even in tachycardias with very circuitous and delayed conduction times. Therefore, minimizing "partial acceleration" will facilitate tachycardia termination, even with significant conduction velocity slowing associated with the shorter pacing cycle length.

For example, measuring how much time pacing was required to entrain the tachycardia. (e.g. as measured by distant electrodes or by far field morphology changes), this time is the amount of time pacing must be advanced from a given catheter in order to reach the arrhythmia. By knowing the amount of time required to entrain the circuit, the anti-tachycardia pacing algorithm can be optimized. This can be used to determine how many paced beats to initiate and the pacing interval(s) to use. The pacing intervals can be adjusted such that the entrance site is activated at the same time the native arrhythmia meets the entrance site. The following stimulated wavefront can be delivered to excite the arrhythmia circuit at a shorter pacing interval. However, as previously mentioned, this tissue can be optimized by the prior pacing intervals to accept the shortest possible pacing interval. This interval can be mathematically calculated and then optimized based on the time required to entrain the tachycardia. This pacing interval after the initial entraining stimulations can then be gradually shortened until the tachycardia is terminated. Various stimulation morphologies and algorithms can also be used to optimize local capture.

Therefore, we have demonstrated that the timing of tachycardia entrainment can be used to optimize the initial overdrive pacing algorithm. Additionally, it is advantageous to improve the first ATP attempt. When entrainment has been obtained, the depolarized wavefronts from the pacing electrode are able to reach the reentrant circuit. A distal electrode and/or wavefront morphology analyses can often determine when entrainment has been obtained and also if the tachycardia has been terminated. This concept is discussed extensively in the supplemental figures.

After obtaining entrainment, the pacing electrode can deliver a single or multiple stimulations at the original tachycardia cycle length. If this occurs, the pacing wavefront will reach the reentrant circuit at approximately the same time as the native wavefront traveling in the reentrant circuit. Importantly, when pacing close to the tachycardia cycle length, the tachycardia cycle length determines the repolarization rates within the tachycardia circuit. Therefore, an ATP attempt can deliver stimulations at a slower cycle length (such as the original tachycardia cycle length) in order to delay the rate of repolarization. For example, an ATP attempt may deliver eight stimulations at PCL1. Far-field morphology and a distal electrode identify the tachycardia has been entrained. The ATP algorithm can now deliver one or several pacing stimulations at the original tachycardia cycle length. This slower rate will delay the rate of tissue repolarization; however, pacing maintains access the pacing electrode has with the reentrant tachycardia. The ATP algorithm can then deliver a single or several stimulations at a shorter cycle length that rapidly and completely accelerates the tachycardia. Far-field morphology and the distal electrode can identify if the tachycardia has been terminated. If the tachycardia has not been terminated, the device can deliver a single or several stimulations at the tachycardia cycle length, followed by a single or several stimulations at an even shorter cycle length than the previous attempt. This pattern can be repeated at shorter and shorter cycle lengths until the tachycardia is terminated. In this manner, only a single ATP attempt is required to terminate the tachycardia and also improves the ability to terminate the tachycardia at any given paced cycle length.

Additionally, as previously discussed, the post-pacing interval, far-field morphology analyses, and timing of signals from a distal electrode in response to overdrive pacing can all be used alone or in combination with other methods to estimate the amount of conduction delay within the tachycardia circuit. This conduction delay can be added to the 'priming' stimulation, such that a single pacing stimulation at the tachycardia cycle length plus the amount of tachycardia delay is delivered after entrainment has been obtained. The priming stimulation slows the repolarization time within the tachycardia circuit while maintaining access for the pacing location to reach the reentrant circuit. After the priming stimulation, an additional pacing stimulation with a shorter pacing cycle length can then be delivered with a greater probability of tachycardia termination. Furthermore, tachycardia termination, entrainment, and conduction delay within the reentrant circuit can be estimated in order to deliver additional 'priming' stimulations followed by a shorter stimulation. In this manner, the ATP algorithm is reactive in the sense that responses from overdrive pacing are utilized in order to optimize the ATP attempt. This process can also be repeated to facilitate tachycardia termination. Sensing the timing of entrainment or tachycardia termination can sometimes be difficult when the sensed time falls near the stimulation time. By having numerous electrodes (such as a quadripolar left ventricular cardiac resynchronization lead), the various electrodes can increase the probability the appropriate window for tachycardia assessment (both entrainment and termination) will be present. By recording the success prior ATP attempts have had in terminating the defined tachycardia, repeating of a successful pacing algorithm can be performed; or, if unsuccessful, the paced cycle lengths can be shortened.

A distal electrode and far-field morphology may or may not identify entrainment and/or tachycardia termination. These abilities are dependent on a number of details specific to the tachycardia including spatial relationships between electrodes and the native tachycardia and conduction properties within the myocardium. Fortunately, bi-ventricular pacing systems usually incorporate two electrodes, which are distant from each other. Having two electrodes distant to each other across the myocardium increases the probability that these electrodes will be able to determine the timing of tachycardia entrainment, tachycardia termination, and the amount of time delay within the reentrant tachycardia.

One exemplary embodiment describes far-field morphologies, tachycardia rates, and timing differences between electrodes to identify various reentrant tachycardias a patient may have. By accurately identifying the varying reentrant tachycardias, prior ATP failures and attempts can used to optimize subsequent ATP attempts.

In yet another embodiment, a second distal electrode within the heart can be used to monitor the ATP attempt. Time changes in the tachycardia cycle length during pacing are used to adjust the next stimulated pacing cycle length. Once entrainment has been verified, the ATP algorithm can deliver one or more stimulations close to the baseline tachycardia cycle length plus some percentage of the measured time delay within the circuit (or a function related to one or both measurements), followed by one or more stimulations at a shorter pacing cycle length. The long pacing cycle lengths serve to 'prime' the reentrant tachycardia to prolong repolarization times in order to facilitate tachycardia termination. With persistent pacing, the shorter cycle length may cause conduction delay within the reentrant tachycardia. The premature pacing gradually propagates through the areas of conduction decrement until all of the myocardium in the chambers of interest have the same interval. After delivery of the "priming" stimulation, the repolarization rates prolong throughout the myocardium. Delivery of a pacing cycle length at a shorter cycle length is therefore at increased probability to reach myocardial tissue that is refractory, particularly in areas critical to maintain the reentrant tachycardia. Many tachycardias will experience conduction slowing "time delay" within critical aspects of the reentrant tachycardia prior to tachycardia termination. Therefore, by careful monitoring of far-field morphology or additional electrodes not involved in pacing, the processor can monitor for conduction slowing within critical aspects of the tachycardia. The device can therefore monitor the time delay occurring within the tachycardia. As long as the time delay continues to prolong, the processor continues to deliver pacing pulses at largely the same pacing interval. However, if the time delay is stable within a specified interval, the device can proceed with next steps of the anti-tachycardia pacing algorithm (such as delivery of a shorter pacing cycle length or delivery of a 'priming' pacing pulse). We describe methods where tachycardia entrainment, conduction delay, and/or tachycardia termination are estimated and used to optimize subsequent pacing cycle lengths.

FIG. 1 reveals a schematic diagram of a pacemaker/implantable cardio-defibrillator (ICD) with specialized leads going into the heart in which the present invention may be usefully practiced. In the embodiment shown in FIG. 1, there is a controller 40 designed to be implanted into the body. The housing 42 of the device is connected to several leads that are designed to be implanted into the patient's heart 90. The first lead 10 may include a proximal end 12 coupled to the housing 42 and a second end sized for introduction into the patient's heart 90, e.g., into the right atrium 92. The first lead may have a distal end 16 connected to a sensor and/or electrode 18 which can sense electrical activity (depolarizations) and pace the right atrium 92, as programmed. In addition, the distal end of the first lead 10 may include one or more features, e.g., a screw tip or other anchor (not shown) on the distal end for securing the distal end relative to the right atrium 92 or left atrium (not shown). One or more wires or other conductors may extend from the distal end to the proximal end to communicate the signals from the sensor 18 to the controller 40. Similarly, the second lead 20 may include a proximal end 22 coupled to the housing 42 and a second end sized for introduction into the patient's heart 90, e.g., into the right atrium 92, through the tricuspid valve 95 and into the right ventricle 96. The second lead 20 contains a distal end 26 which may contain an electrode and/or sensor 28 designed to sense electrical activity or deliver electrical energy to stimulate the right ventricle 96. Similar to the first lead 10, the second lead 20 may include one or more features, e.g., a screw tip or other anchor, on the distal tip to secure the distal end within the patient's heart 90, e.g., the wall of the heart 90 within the right ventricle 96, similar to pacing leads. Alternatively, the first and second leads may be provided on a single device with a branch distal end (not shown), similar to other embodiments herein. Additionally, there may be a third lead 30 with a proximal end 32 in order to couple the lead to the housing 42. The third lead may contain a second end sized for introduction into the patient's heart 90, e.g., into the right atrium 92, through the coronary sinus 97 or other vein of the heart 90. This lead may contain a sensor or electrode 34 designed to sense or deliver electrical activity. This sensor or electrode 34 may sense and/or deliver electrical activity to either the atrial or ventricular tissue. In addition, the third lead 30 may contain a distal end 36 coupled to an additional sensor or electrode 38 to sense and deliver electrical activity to a different location in the heart 90. Similar to the first lead 10 and second lead 20, the third lead 30 may include one or more features, e.g., a screw tip or other anchor, on the distal tip to secure the distal end within the patient's heart 90, e.g., within a distal vein of the coronary sinus 97, similar to typically used pacing leads. This lead may sense and pace electrical activity occurring in the left ventricle 98. In addition, if there is a tachycardia occurring within the right ventricle 96 or the left ventricle 98, the sensors or electrode 28, 34, or 38 may sense and/or deliver electrical activity in order to terminate the tachycardia. In addition, if there is a tachycardia occurring within the right atrium 92 or left atrium (not shown), the sensors or electrodes 18 or 34 may sense and/or deliver electrical activity to terminate the tachycardia. The electrodes 18, 28, 34, or 38 are used to illustrate the delivery of anti-tachycardia pacing (ATP) therapy throughout this description, although any number of electrodes are capable of sensing and delivering electrical energy to the heart 90. The ATP therapy may be used to treat ventricular as well as atrial tachyarrhythmias.

Figure 2:
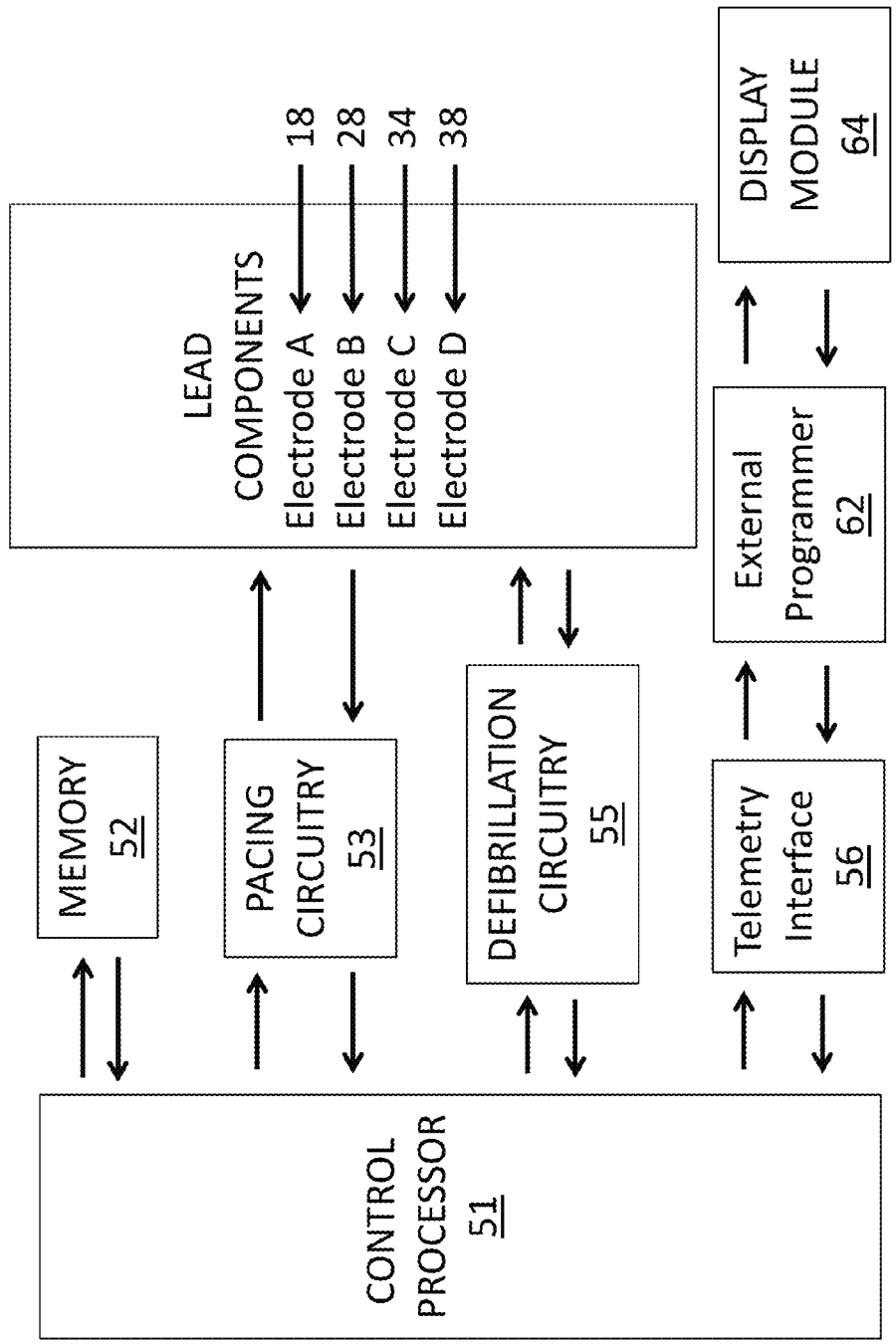
FIG. 2 is a functional block diagram of the circuitry located in the implantable pacemaker/cardioverter/defibrillator of FIG. 1.

FIG. 2 shows a simplified functional block diagram of one embodiment of the components located within and connected to the controller 40. The components include a control processor 52 which receives input information from various components in order to determine the pacing algorithm in order to treat the patient. The control processor is connected to pacing circuitry 53, defibrillation circuitry 55, memory 52, and a telemetry interface 55. The pacing circuitry 53 and the defibrillation circuitry 55 connects to the first lead 10, second lead 20, and third lead 30; and ultimately connects to the electrodes, (for example, 18, 28, 34, and 38). These connections allow for multiple capacities to sense electrical activity (such as myocardial depolarizations), deliver pacing stimulations, and/or deliver defibrillation or cardioversion shocks. Based on the input received from the electrodes 18, 28, 34, and 38 through the pacing circuitry 53, the control processor 51 performs calculations to determine the proper course of action, which may include providing ATP therapy to one or more electrodes, providing defibrillation or cardioversion shocks to one or more electrodes through the defibrillation circuitry 55, or no therapy at all. The control processor 51 is connected to a telemetry interface 96. The telemetry interface can wirelessly send and receive data from an external programmer 62 which is coupled to a display module 64 in order to facilitate communication between the control processor 51 and other aspects of the system external to the patient. The control processor 51 may continue to sense electrical activity from one or more electrodes while deliver pacing stimulations to other electrodes. The control processor 51 may store selected data to memory 52, and retrieve stored data as necessary. For example, the control processor 51 may identify key aspects of a tachyarrhythmia in order to effectively differentiate the tachycardia and other key aspects of the tachyarrhythmia in order to optimize the best therapy in order to terminate the tachyarrhythmia.

Figure 3:
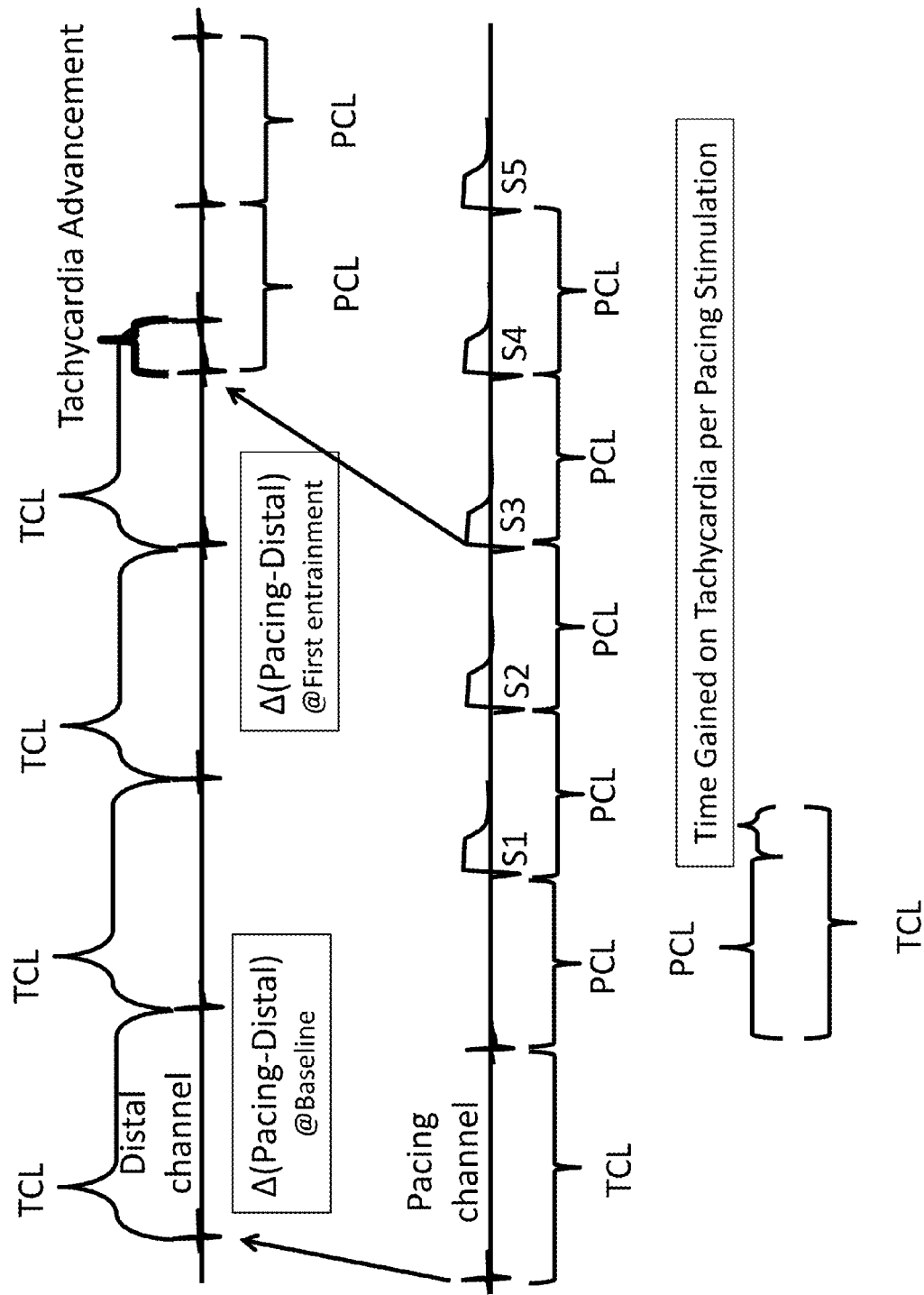
FIG. 3 is a graphical representation of overdrive pacing from one electrode while sensing electrical depolarizations from a second electrode. The Fig helps demonstrate how timing measurements can be performed to estimate the Time to Entrainment.

FIG. 3 is a graphical representation of overdrive pacing from one electrode while sensing electrical depolarizations from a second electrode. The Fig helps demonstrate how timing measurements can be performed to estimate the Time to Entrainment. The time to entrainment is the total amount of time overdrive pacing must 'gain' on the native tachycardia in order to reach and then accelerate the tachycardia. Therefore, as demonstrated in FIG. 3, the time to entrainment can be estimated by measuring the timing of sensed electrical activity on a second, distal electrode. For example, if a tachyarrhythmia occurs between two electrodes inside of a heart, one electrode may deliver ATP. As soon as the delivered electrical activity creates a depolarizing wavefront that reaches and accelerates the native tachycardia, the second electrode can determine this event. In this event, for example, the time to entrainment can be estimated by adding the prematurity of each paced stimulation (TCL−PCL) minus the amount of tachycardia acceleration. Therefore, the time to entrainment can be estimated as the (TCL−PCL) times the number of pacing stimulations required to entrain the tachycardia minus the amount of tachycardia acceleration on the first entrained stimulation. There may be delay in the tachycardia due to the shorter paced cycle length. This delay can be estimated by slowing the overdrive pacing cycle length, for example the paced cycle length can be prolonged to approximate the tachycardia cycle length. Another method to estimate the time to entrainment is by summing the difference in time between the paced stimulations and the sensed depolarizations. Again, conduction delay needs to be taken into account.

Another method involves measuring the difference in time before pacing and during entrainment (or the first entrainment) between the pacing electrode to the sensing electrode. This time difference is similar to the time described by the N+1 difference (Soejima et al, 2001).

In yet another embodiment, the time to entrainment can be estimated by the return cycle of a failed ATP attempt minus the tachycardia cycle length. The return cycle can also be measured by a specific pacing maneuver designed to determine the time to entrainment while minimizing conduction delay within the circuit. For example, the ATP pacing algorithm may deliver a number stimulations until entrainment would likely to have occurred or with evidence of entrainment; followed by deliver of pacing stimulations at a cycle length approximating the tachycardia cycle length. When pacing close to the tachycardia cycle length, the time delay between the stimulation to the sensed electrical depolarization (or far-field morphology analyses demonstrated in FIG. 4) can be used to estimate the time to entrainment. Alternatively, ATP can be stopped; and the resulting post-pacing interval (PPI) or the return interval can be measured to estimate the entrainment time by calculating the PPI minus the tachycardia cycle length. As previously mentioned, the Time to Entrainment can also be estimated by two entrainment maneuvers by electrodes on opposite sides of the reentrant circuit. Of note, as demonstrated in FIG. 3, the third stimulation brings in the sensed depolarization sensed by the sensing electrode. The next interval seen on the sensing electrode has an interval equal to the PCL. This demonstrates that any delay that may have occurred in the paced stimulation on the first entrained stimulation was similar on the second entrained stimulation. However, if the interval measured on the sensing electrode were longer than the PCL, this delay would suggest conduction delay along the path between the pacing electrode and sensing electrode. This embodiment is discussed in more detail in FIG. 10; where this time delay may be utilized to adjust the pacing algorithm in order to facilitate tachycardia termination.

FIG. 4A and FIG. 4B reveal an example of intracardiac and far-field morphologies which illustrate how far-field morphology analyses can be utilized to estimate the Time to Entrainment. FIG. 4A reveals the far-field morphology occurring in three different scenarios. The first column demonstrates the far-field morphology occurring when pacing at baseline (when no underlying tachycardia is present). The second column reveals far-field morphology occurring during a tachycardia. In this figure, the timing of the sensed depolarization occurring on the electrogram can be determined in relation to the far-field morphology. In the third column, the entrained far-field morphology is shown. In FIG. 4B, the far-field morphologies are superimposed such that the waveforms overlap. Various computational algorithms and programs can be performed to determine the various off-set required to minimize the difference between waveforms. In yet another embodiment, the waveform analyses can determine the offset required such that the sum of the baseline paced morphology and the baseline tachycardia are arranged such that the sum of these waveforms approximate the entrained tachycardia. When this occurs, the time offset between the paced stimulation and the sensed depolarization on the pacing electrode can be used to estimate the Time to Entrainment. As previously mentioned, this time can be used to optimize the pacing algorithm. Furthermore, with continued pacing, the off-set may prolong indicative of conduction delay occurring within the path of electrical conduction.

Figure 5:
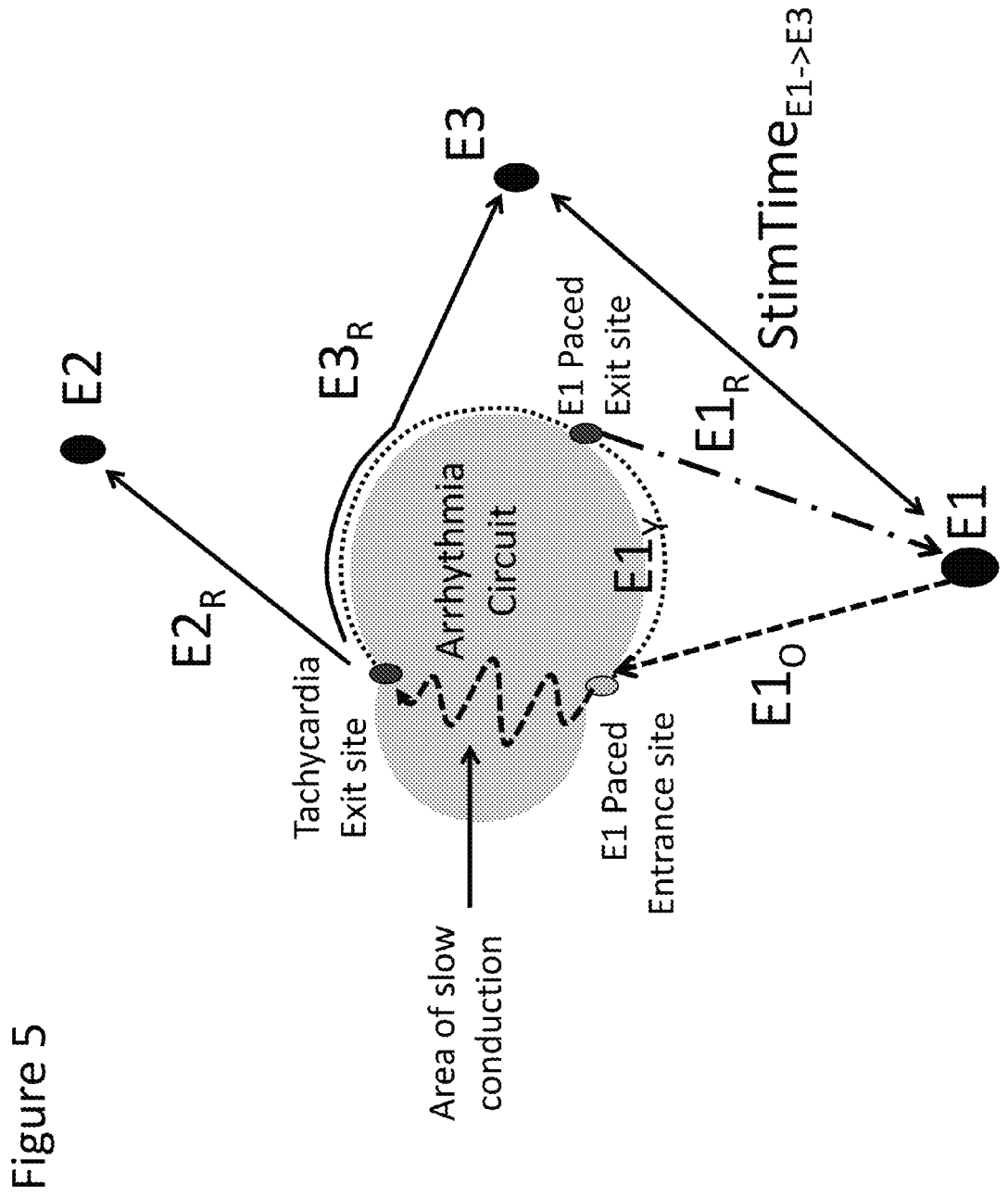
FIG. 5 is a simplified diagram of a reentrant tachycardia circuit within a heart and several pacing electrodes for sensing and/or delivering electrical stimulations according to an exemplary embodiment.

FIG. 5 a simplified diagram of a reentrant tachycardia circuit within a heart and several pacing electrodes for sensing and/or delivering electrical stimulations according to an embodiment of the present invention. This figure demonstrates a key concept in utilizing more than one electrode to optimize ATP algorithms. In this figure, the plane of the figure represents myocardial tissue capable of propagating depolarizing wavefronts. In this embodiment, there are three electrodes, E1, E2, and E3, each capable of sensing and delivering electrical activity. There is a scar between the electrodes that does not conduct electrical activity. Additionally, there is a an area of slow conduction, within the scar, that is able to conduct electrical activity, but slower than the other, healthier, myocardial tissue. In this example, a reentrant tachycardia can be created which is capable perpetual circular movement through the area of slow conduction and then around the scar. When an electrode obtains tachycardia entrainment, for example, electrode E1, the Time to Entrainment, is roughly the time it takes for the paced stimulation to leave the pacing location (Time $E1_O$) to the "entrance site," plus the time it takes for electrical activity to leave the native circuit from the "exit site" to the pacing location (Time $E1_R$), minus the time it takes to travel in the tachycardia circuit between the exit site and the entrance site (Time $E1_T$). Therefore, the Entrainment Time for electrode E1 is roughly $E1_O+E1_R-E1_T$. During pacing at an unchanging pacing cycle length, there will be fusion between the wavefront created from the pacing location and the wavefront created when leaving the tachycardia exit site. These wavefronts collide at various locations depending on circuit morphology, conduction velocities, and other variables. Prior to the tachycardia, the time it takes to conduct electrical signals from one electrode to the others can be measured. For example, pacing from electrode E1 will be sensed by electrodes E2 and E3; and the time delay between stimulation and sensing the depolarizations from these other electrodes can be measured. Given conduction velocities can be variable depending on the pacing cycle length; these time delay can be recorded at various cycle lengths and therefore not necessarily constant. When entrainment has been obtained, the location of wavefront collision (aka fusion) is dependent on a number of variables including the tachycardia cycle length and the pacing cycle length. If entrainment is obtained but the wavefront from the stimulating electrode reaches the distal electrode, this electrode will not be able to determine the timing of entrainment or the Time Delay that may occur in the circuit. The system therefore can measure the baseline conduction time that is required to travel from the pacing electrode (E1) to any other electrode (EX): $StimTime_{E1 \to EX}$. In addition, during the tachycardia, the time delay between the sensed signals occurring between the electrode that will pace (E1) and any other electrode (EX) can be measured during the tachyarrhythmia: $ReentrantTime_{E1 \to EX}$. The ability of a distal electrode EX to determine the timing of entrainment (as well as Time Delay in the circuit), can be estimated by equation 7 below. The Reentrant Time is the difference in time to leave the exit site and travel to both the pacing electrode E1 and any other electrode EX.

Cannot verify entrainment if:

$$\text{Time to entrainment}-(TCL-PCL)-\text{Time Delay} > \text{Stim Time}_{E1 \to EX}-\text{Reentrant Time}_{E1 \to EX} \quad (7)$$

Therefore, by having more than two electrodes, the probability of having an electrode capable of sensing entrainment is increased. Furthermore, even when the electrode satisfies equation 7; the timing of sensing local signals can be missed [blanked] if the sensing occurs simultaneously with the timing of pacing. Therefore, additional electrodes, even close in proximity, can augment the probability the timing of entrainment can be determined, as well as estimation of Time Delay within the circuit. Furthermore, if the pacing entrance site is close in proximity to the tachycardia exit site, far-field morphology analyses may be limited in its ability to estimate the Time to Entrainment and potential Time Delay. With one or more distal electrodes capable of measuring the entrained tachycardia, the system can estimate entrainment, time delays in the circuit, and tachycardia termination. By correctly measuring and/or estimating these components, ATP pacing algorithms do not need to stop pacing until the tachyarrhythmia is terminated. This describes another example in which ATP algorithms can be optimized to more rapidly and efficiently terminate tachyarrhythmias.

In yet another embodiment, the system may be able to design the initial anti-tachycardia pacing algorithm based on some measurements. For example, by recording the baseline conduction time from the pacing electrode to at least one additional electrode, and measuring the difference in time between these two electrodes during an episode of tachycardia, the Time to Entrainment may be estimated as the difference of these measurements. This method requires certain assumptions regarding the reentrant circuit and its relationship to the pacing electrodes; however, this method creates a rapid initial ATP algorithm that has a high probability of tachycardia termination. In yet another embodiment, having the device routinely measure conduction times between electrodes, the device may monitor and assess for ischemic episodes. This is because ischemia can change conduction times. Therefore, during a myocardial infarction, the conduction times may change. Therefore, monitoring conduction times may serve as an indicator of ischemia and can alert the patient or care-takers to take action.

Figure 6:
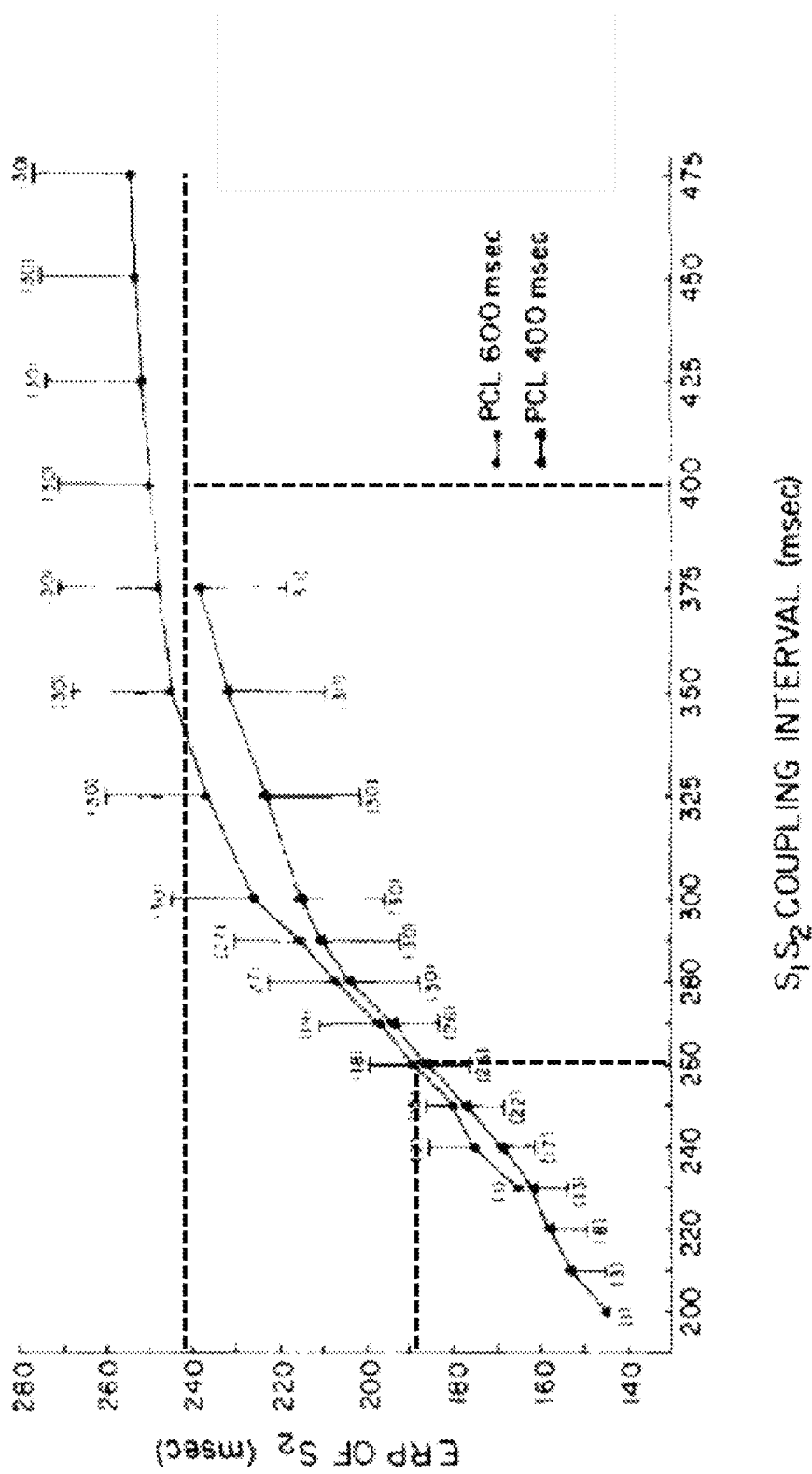
FIG. 6 reveals the relationship between the coupling intervals during a pacing drivetrain and the effective refractory period, also known as the electrical restitution curve.

FIG. 6 reveals the relationship between the coupling intervals during a pacing drivetrain and the effective refractory period, also known as the electrical restitution curve. FIG. 6 demonstrates a typical electrical restitution curve seen in ventricular myocardial tissue. In this figure, a pacing train was performed at two cycle lengths, 400 ms and 600 ms. Then, a coupling stimulation was delivered at various intervals (x-axis) which was followed by a second stimulation S2. The coupling interval predicts the interval of the second stimulus that fails to capture the myocardium (the effective refractory period or ERP). Note how significantly a single coupling interval dramatically affects the ERP of the second premature stimulus. For example, when deliver a pacing train at 400 ms, a single stimulus at 230 ms is refractory (does not conduct) in the majority of patients. However, if a pacing train is delivered at 400 ms, followed by a coupling interval of 260 ms, the stimulus at 230 ms no longer is refractory for any of the patients in this study. In order to terminate the majority of patients, the second stimulus needs to shorten by over 40 ms, and stimulate at less than 190 ms in order to reach refractoriness. The electrical restitution curve reveals how dramatically repolarization rates are determined by the previous depolarization interval.

Figure 7:
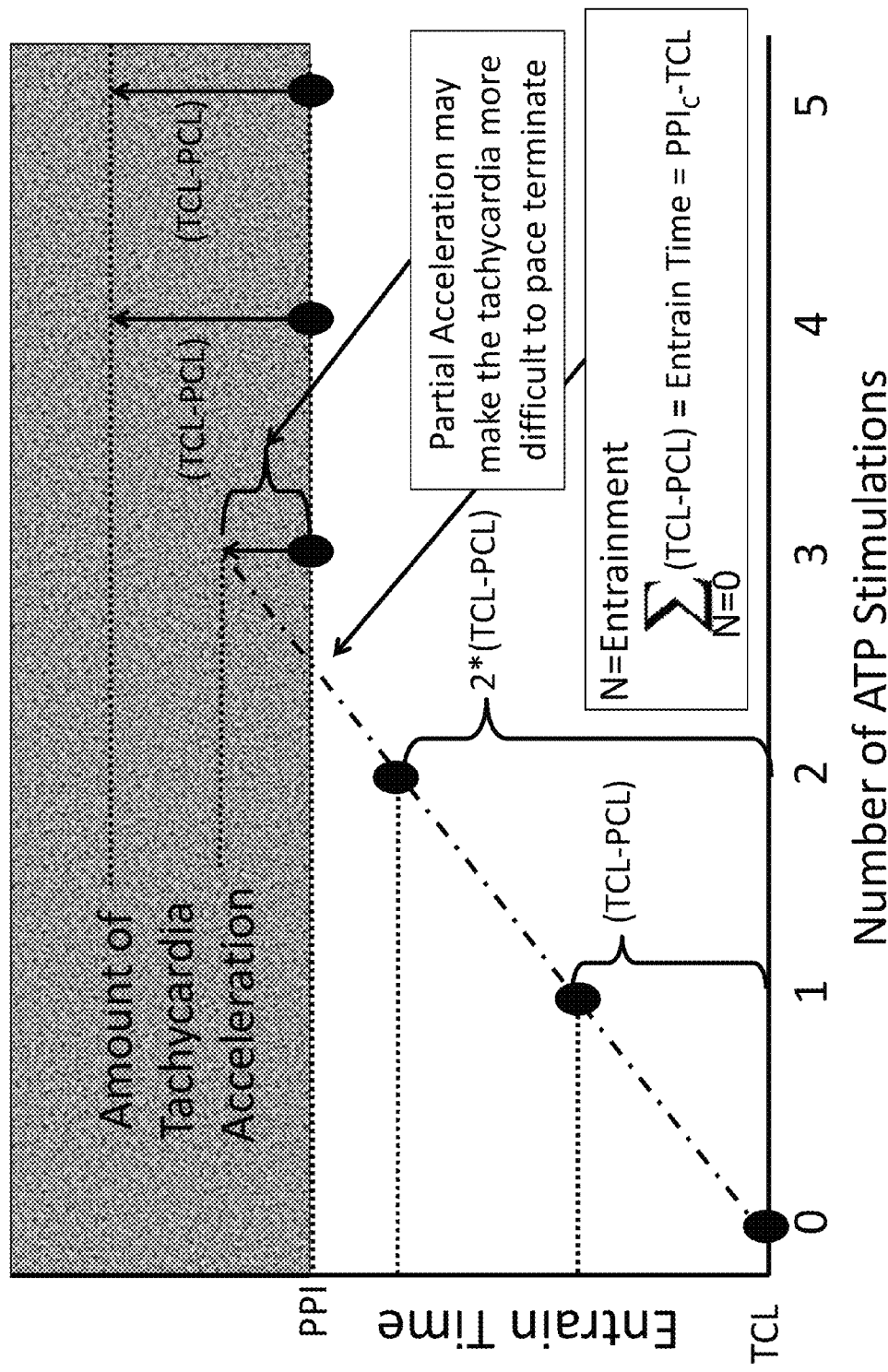
FIG. 7 is a graphical representation explaining how the paced cycle length and number of stimulations affects the amount of tachycardia acceleration on the first entrained stimulation.

FIG. 7 is a graphical representation demonstrating the relationship between the pacing prematurity (TCL−PCL), the number of pacing stimulations, the Time to Entrainment, and the amount of tachycardia acceleration on the first entrained stimulation. This figure demonstrates the importance the electrical restitution curve in designing ATP algorithms. In order to 'gain' on the native tachycardia, ATP must pace faster than the TCL. Each paced stimulation gains on the tachycardia by the difference between the TCL and the PCL (the "pacing prematurity). ATP or overdrive pacing begins to accelerate the tachycardia when the sum of the pacing prematurity is greater than the Time to Entrainment. The first stimulation that accelerates the tachycardia, however, can shorten the TCL by any amount between the TCL and the PCL. With perpetual pacing, the entire tachyarrhythmia will accelerate to the PCL; however, the first stimulation that entrains the tachycardia may only partially accelerate to the PCL. Since the goal of ATP is to reach electrical refractoriness within the reentrant circuit; this partial acceleration can prepare the tissue involved in the reentrant circuit to repolarize more quickly. Based on mathematically modeling and empirical testing, the amount of acceleration on the first entrained stimulation will dramatically effect whether or not the tachyarrhythmia is terminated at any given PCL. With knowledge of the Time to Entrainment, the prematurity can be arranged such that the first stimulation that accelerates the tachycardia will accelerate the tachycardia to the desired PCL. This arrangement can minimize the partial acceleration occurring on the first entrained stimulation; and help optimize the probability of tachycardia termination.

Figure 8:
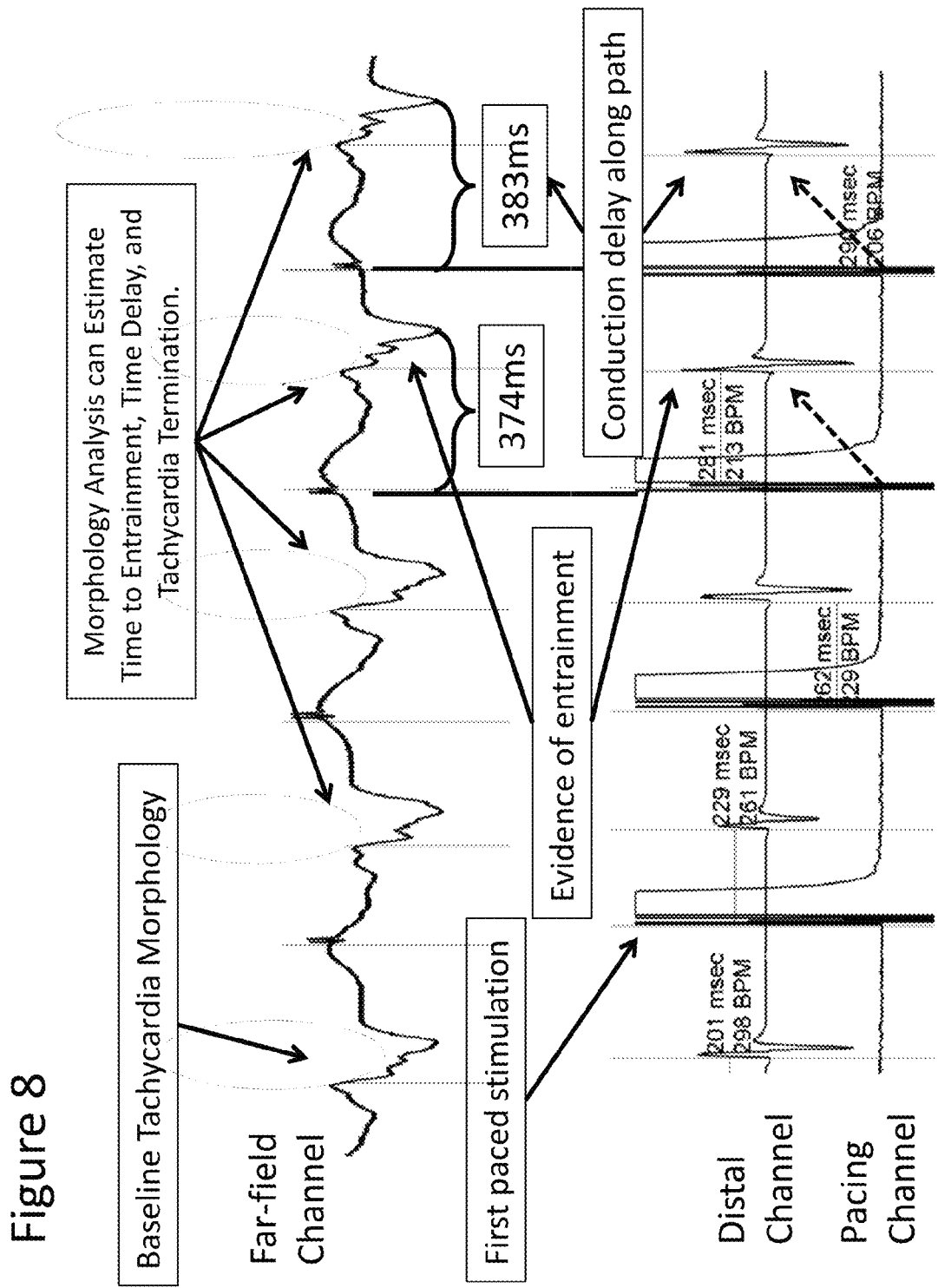
FIG. 8 reveals an example of utilizing intracardiac measurements and far-field morphology analyses to determine the Time to Entrainment and TIME Delay within the circuit taken from an ATP attempt from an epicardial electrode.

FIG. 8 reveals an example of utilizing intracardiac measurements and far-field morphology analyses to determine the Time to Entrainment and Time Delay within the circuit taken from an ATP attempt from an epicardial electrode. In this example, two electrodes are located on roughly opposite sides of a reentrant tachycardia. Pacing is initiated, and the third stimulation reveals the signal was brought in on the distal electrode channel. As discussed previously in relation to FIG. 3, various measurements can be performed at this point to estimate the Time to Entrainment. Furthermore, far-field morphology analysis revealed (as previously discussed in FIG. 4) the overlapping time gain to accelerate by less than predicted by the difference between the TCL and PCL; and therefore the entrainment time can be estimated. Furthermore, as can be seen in the figure, the fourth stimulation also entrained the reentrant tachycardia, however, the stim to sense timing prolonged from 281 ms to 290 ms. On far-field morphology, the stim to far-field minimum also prolonged by 9 ms. Therefore there was 9 ms delay somewhere between the pacing electrode and the sensing electrode, usually in areas of slow conduction. These areas of slow conduction usually occur at critical aspects of the reentry tachycardia. In one embodiment (which may be programmable), the device can sense this delay in conduction and continue pacing as long as conduction delay continues to prolong from overdrive pacing (as evidenced from far-field morphology analyses or at least one additional electrode). The device can therefore estimate and record the Time Delay that is occurring.

Figure 9:
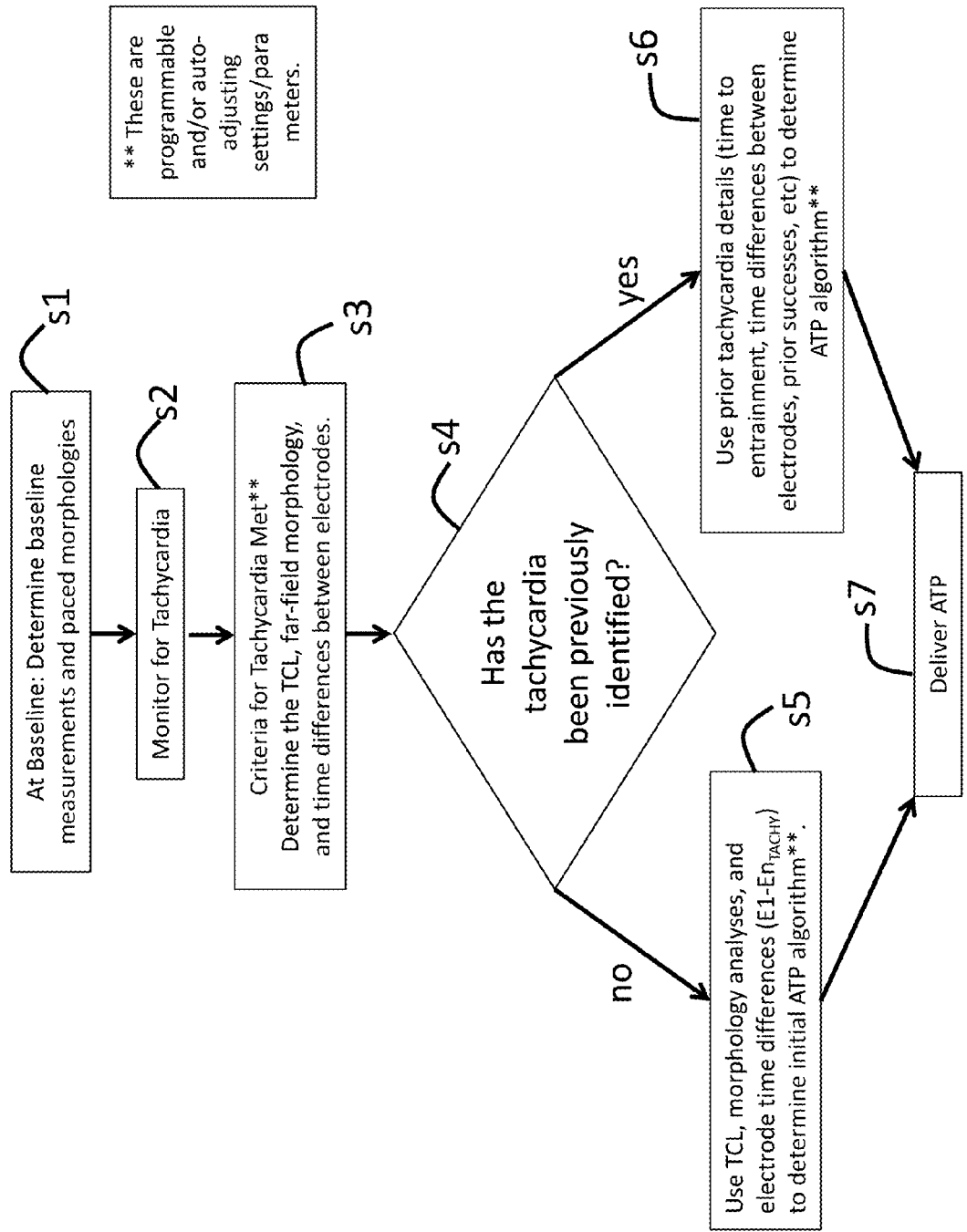
FIG. 9 is a flow diagram illustrating an exemplary process for applying an ATP therapy according to an exemplary embodiment utilizing prior ATP attempts, return cycle intervals (aka post-pacing intervals), far-field morphology analyses, and/or at least one additional electrode.

FIG. 9 reveals a flow chart of one embodiment to determine the ATP therapy. In Step 1, the device assesses and records the baseline conduction times to various electrodes and pacing morphologies from one or more of the electrodes when the patient is not in tachycardia. These measurements are used for reference when determining if ATP therapies are able to determine entrainment from additional electrodes or far-field pacing morphology analyses.

In Step 2, the device is programmed to monitor for tachycardia. In Step 3, the device determines the patient is now in a tachyarrhythmia. The criteria of determining criteria for tachycardia have been previously described. In addition, using the timing differences between more than one electrode; and the timing differences between far-field morphology analyses and local activation can help identify and mathematically describe tachyarrhythmias. Additionally, these specific measurements can be recorded and used to identify and differentiate tachyarrhythmias. Later in the algorithm, the device can record the Time to Entrainment from one or additional electrodes and record the Time to Entrainment for a specific electrode for a specific tachyarrhythmia.

In Step 4, the device assesses whether the newly identified tachyarrhythmia has been previously identified. As mentioned, this is determined by comparing time differences and morphology analyses. If the tachycardia has not been previously identified, we move to Step 5, where the initial ATP algorithm is determined based on the tachycardia cycle length and timing differences between electrodes. For example, the ability to determine entrainment is related to the difference in time between the sensed local activation and the paced time delays between electrodes. The device could determine which electrodes have the greatest probability of being located on opposite sides of the reentrant circuit. In addition, the device may be programmed to deliver ATP from the latest (or earliest) local activation or in relation to baseline timing differences.

If the original tachycardia had been previously identified, we move from Step 4 to Step 6. In this Step, previously successful and unsuccessful ATP attempts can be incorporated into the device to determine the first ATP pacing algorithm. In addition, as previously discussed, recorded Time to Entrainments for this particular tachycardia can be used such that the pacing prematurity is arranged such that the first pacing stimulation to accelerate the native reentrant circuit fully accelerates the reentrant circuit by the difference between the TCL and the chosen PCL. In this manner, partial acceleration is minimized. The first stimulation that accelerates the tachycardia can be shortened if prior attempts failed to terminate on the first accelerating stimulation. In addition, if the first stimulation attempting to accelerate/terminate the tachyarrhythmia fails to capture, the pacing prematurity can be arranged to facilitate local capture. This can be done by gradually increasing the pacing prematurity as a way of 'priming' local myocardium to accept the shorter paced cycle length.

Regardless of the ATP pacing algorithm, both Step 5 and Step 6 move to Step 7 and deliver the ATP as programmed. Timing delays from distal electrodes, far-field analyses, and evoked potentials can be used to determine local capture. Additionally, the return cycle can be used to determine if the pacing stimulations captured the myocardium. Additionally, the exact stimulation which did not capture the myocardium can be identified and used to adjust the ATP pacing strategy.

Figure 10:
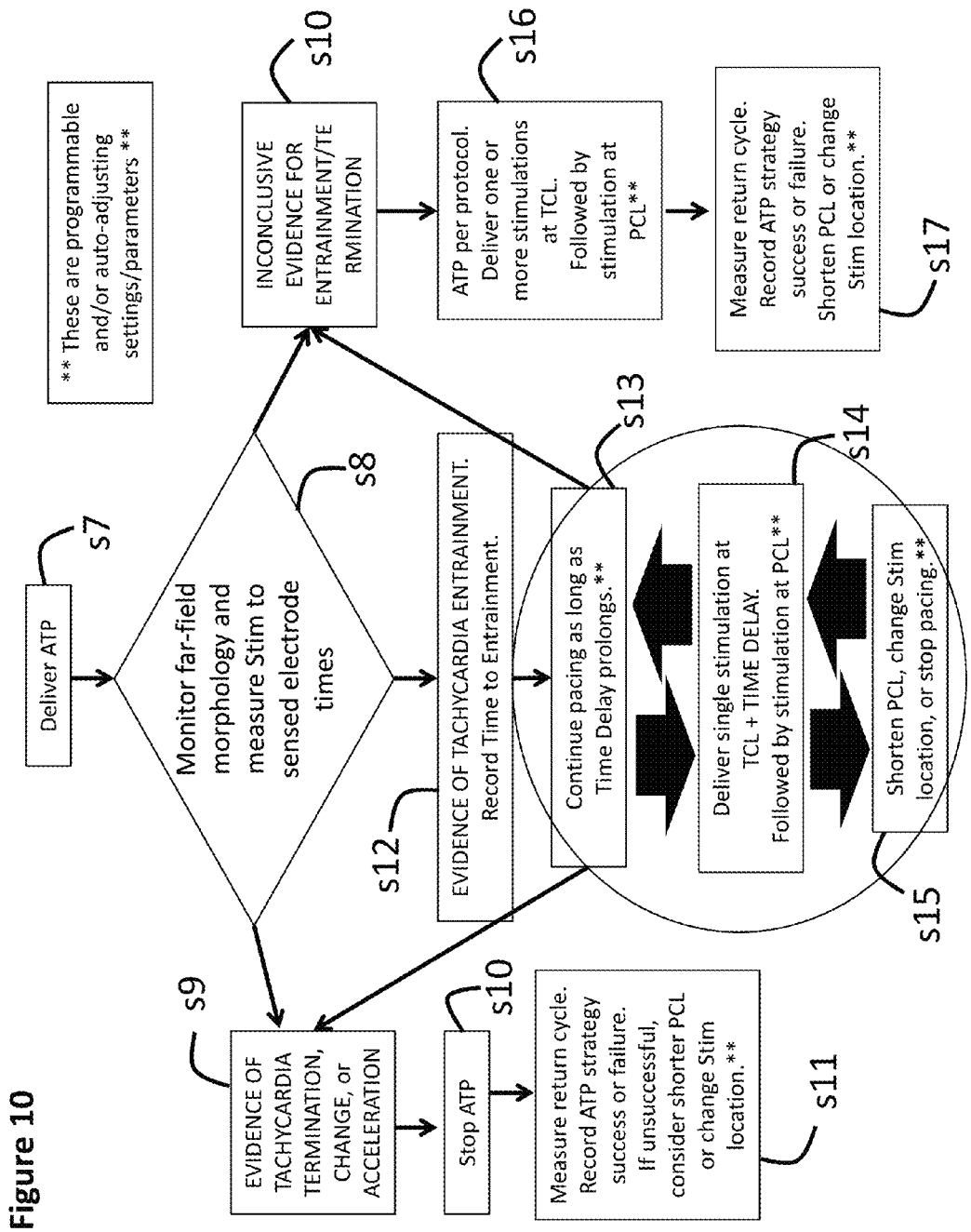
FIG. 10 is a flow diagram further illustrating an exemplary process for applying an ATP therapy according to an embodiment in the present invention utilizing prior ATP attempts, return cycle intervals (aka post-pacing intervals), and/or far-field morphology analyses.

FIG. 10 further reveals a flow chart of one embodiment that may occur once the device delivers ATP in Step 7. At Step 8, the device may monitor and/or perform far-field morphology analyses and the time measurement from the timing of stimulation to local capture measured from electrodes. Until entrainment occurs, these measured times should prolong by the pacing prematurity unless the stimulated wavefront time directly reaches the electrodes. This time measurement, as previously described, is recorded prior to the patient going into the tachyarrhythmia. Therefore, the device can determine if the measured premature signal occurs from direct signal propagation versus the entrained wavefront from the native tachycardia. In Step 9, during an ATP attempt, the device is constantly assessing for evidence of tachycardia termination, a significant change in the tachyarrhythmia, or tachycardia acceleration. If either of these circumstances are met, the device may stop pacing and re-assess the rhythm as in Step 10. Tachyarrhythmia termination, change, or acceleration may be monitored by far-field morphology analyses and/or the rate and relationship among sensed signals from various electrodes.

In Step 11, once the ATP is stopped, the device will measure the return cycle length, determine if the patient remains in a tachyarrhythmia, categorize the most recent pacing strategy was successful or unsuccessful at terminating the tachyarrhythmia. If unsuccessful, the device may shorten the pacing cycle length (PCL) to be more aggressive or change the pacing location depending on the settings programmed into the device.

Now moving back to Step 8, the device may obtain evidence that the ATP attempt has successfully entrained the tachyarrhythmia as in Step 12. At this point, the device will estimate the Time to Entrainment for this identified tachyarrhythmia and use this measurement should this tachyarrhythmia be identified again and attempt to deliver therapy. In one embodiment, the device proceeds to Step 13, where the device continues to deliver pacing stimulations as long as the device measures a prolonging Time Delay. The Time Delay is estimated by a prolongation of stimulation to sensed signal (either from a second electrode or from far-field morphology analyses). The amount of prolongation the device identifies as significant can be preprogrammed and adjustable. Often, however, persistent pacing at a constant cycle length will gradually slow in critical aspects of the arrhythmic circuit and then finally terminate the tachycardia. The first stimulation that does not conduct through the arrhythmic circuit in the orthograde direction can be detected by the device in terms of far-field morphology or a distal electrode as long as the conduction times satisfy equation 7 at which point the device may transition to Step 9.

Once the Time Delay is minimal or less than the programmed determined amount of time, in one embodiment, the device may deliver one or more stimulations at the TCL plus the amount of measured Time Delay as in Step 14. In another embodiment, the device may deliver this priming stimulation at an interval that is determined by the TCL and/or the Time Delay but not necessarily the TCL or the sum of the TCL plus the Time Delay. This priming stimulation prolongs the interval seen by critical aspects of the reentrant circuit while maintaining access to the arrhythmic circuit by the pacing electrode. After delivering one or more priming stimulations, the device can then deliver a pacing stimulation at a shorter pacing cycle length with an increased probability of tachycardia termination. This interval may be the same pacing cycle length (PCL) as the prior pacing stimulation(s) or may be adjusted based on programmable or algorithmic features.

If the tachyarrhythmia does not terminate on this stimulation the device may transition back to Step 13 and continue pacing at the PCL; or the device may proceed to Step 15, where the device may shorten the PCL after the priming stimulation. Alternatively, the device may deliver additional priming stimulations, change the pacing location, or stop pacing altogether. The decision tree can be adjustable based on the TCL and prior attempts. That is, with shorter TCL, the device may be more aggressive by shortening the PCL rapidly. Alternatively, if the tachyarrhythmia is prone to tachycardia acceleration or fibrillation, the device may shorten the PCL more gradually. Each of the steps S13, S14, and S15 are all working in tandem such that the device is delivering ATP while adjusting the ATP based on measured responses from other electrodes or far-field morphology analyses. Furthermore, the device may sense changes in the signals consisted with tachycardia termination (moving to Step 9) or lose the ability to identify termination, in which case the system moves to Step 10.

In Step 10, the timing relationships between electrodes do not satisfy equation 7; or the far-field morphology analyses reveals the pacing morphology (gradual fusion) to match the morphology with isolated pacing in the absence of an underlying tachycardia. This can occur when the tachycardia morphology is similar to the paced morphology from the pacing electrode or when the entrance and exit locations for the entrained tachycardia are close in proximity. In this situation, the device cannot definitively determine when the tachycardia has terminated or accelerated. Therefore, the device must occasionally stop delivery of ATP in order to assess the heart and the rhythm. In these circumstances, the device may move to Step 16, where ATP is driven by protocol. In addition, the device can deliver enough pacing stimulations sufficient to obtain entrainment.

In one embodiment, the device may deliver one or more stimulations close to the TCL ("priming stimulations") followed by one or more stimulations at a shorter cycle length. Alternatively, the device may simply stop ATP and (moving to Step 17), measure the return cycle (the post-pacing interval). This interval can be used to 1) verify the tachycardia was entrained and 2) determine the Time to Entrainment. When the tachycardia requires more than two attempts to pace terminate the tachyarrhythmia, the resulting return cycle length can be measured as well as any Time Delay associated with the shorter cycle lengths. In one embodiment, a priming stimulation utilizing the Time Delay can be delivered to facilitate tachycardia termination even when entrainment cannot be verified during pacing. Again, the Time to Entrainment can be used to arrange the initial pacing stimulations to minimize partial acceleration on the first accelerating pacing stimulation.

After delivering ATP and measuring the return interval, the device can return to Step 2 and assess the tachyarrhythmia. The device can identify if the prior ATP strategy was successful or unsuccessful and use this information to guide the ATP algorithm.

Figure 11:
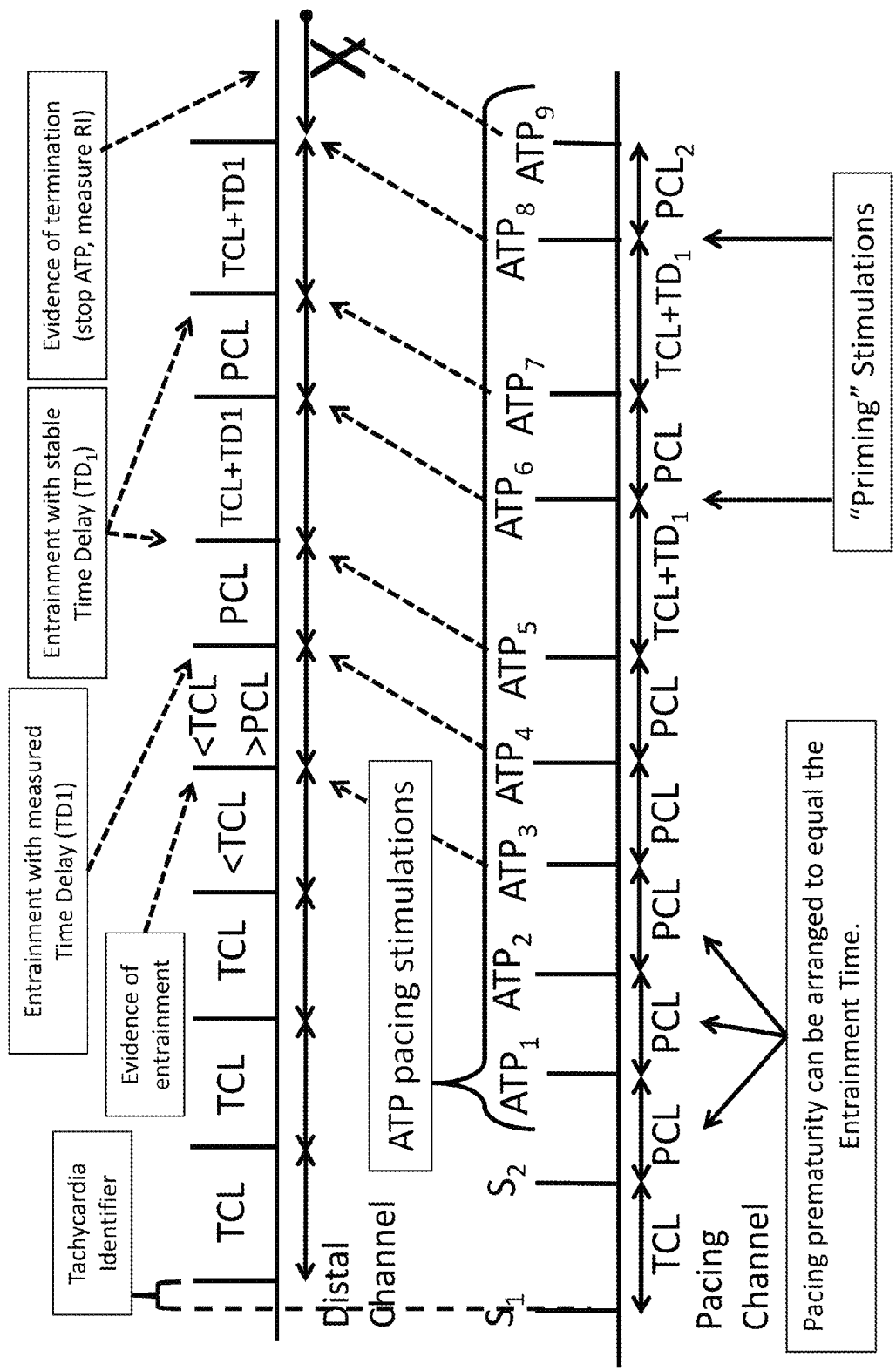
FIG. 11 is a graphical representation of anti-tachycardia pacing (ATP) according to an exemplary embodiment.

FIG. 11 is a graphical representation of deliver an antitachycardia pacing therapy according to one embodiment of the present invention. Depolarizations or signals sensed by the pacing channel electrode are labeled S1 and S2. The distal channel electrode has a line when it senses depolarizations or signals. ATP pulses are labeled with ATP1 being the first pacing stimulation and ATP9 is the last pacing stimulation. The time interval between the first and second sensed signals is the tachycardia cycle length (TCL). The TCL, the timing differences between electrodes, and the far-field morphology (not shown) can be used to identify the tachycardia ("Tachycardia Identifiers"). The sensed signals can alert the Control Processor of the tachycardia and determines the ATP pacing strategy. The device begins delivering ATP pulses. If the Time to Entrainment had previously been recorded for this tachycardia, the device would arrange the initial pacing prematurity such that the sum prematurity is equal to the Time to Entrainment. The following pacing stimulation would then completely accelerate the arrhythmic circuit by the pacing prematurity of that paced stimulation (TCL-PCL).

In FIG. 11, the third pacing stimulation brings in the sensed signal on the distal channel. Assuming this time is shorter than the previously recorded conduction time between these electrodes, this would suggest the tachycardia has been entrained, which may signal to the processor the tachycardia is now being advanced by the pacing stimulations. The pacing prematurities can be summed to the point of tachycardia advancement to estimate the Time to Entrainment; alternatively the difference in time from the Stim to sensed signal on the distal channel between the first entrained stimulation and the baseline tachycardia can be used to estimate the Time to Entrainment. In the graphical representation, note the fourth pacing stimulation should be completely entrained (advanced to the pacing cycle length), however, there is a prolongation in the stimulation to sensed time on the distal channel. This prolongation can be attributed to conduction delay within the myocardium and can be used to estimate the Time Delay (TD1). The fifth ATP pacing stimulation notes a stable Time Delay. Therefore, in one embodiment, the device delivers a "Priming" stimulation, by delivering a stimulation with the interval of the TCL plus the TD1 (or some percentage of the TCL plus the TD1). In yet another embodiment, the device may deliver one or more pacing stimulations at the original tachycardia cycle length or substantially similar to the tachycardia cycle length.

In other embodiments, this "priming" stimulation can deliver one or more pacing stimulations at or near the TCL. The device then delivers a pacing stimulation with a shorter interval. In this example, the tachycardia does not terminate (there is a sensed signal from ATP 7) and there was no measured conduction delay (the interval equals the PCL). Had the device measured a conduction delay, the device could have continued delivering ATP therapy at the same PCL. In the current embodiment, the device delivers a second "priming" stimulation, followed by a PCL at a shorter cycle length (PCL2). In this example, the sensed signal on the distal channel does not sense a signal (the amount of delay deemed significant can be programmed) and therefore can identify the tachycardia as terminated and pacing is stopped in order to assess the rhythm.

Sometimes, the Time Delay measured occurs from conduction changes or circuit changes at locations other than the arrhythmic circuit, for example, near the pacing electrode. In this scenario, delivering priming stimulations at the TCL plus the TD1 will result in loss of entrainment to the arrhythmic circuit. The time interval between the stimulation and the sensed signal on the distal channel can be used to identify and the ATP pacing algorithm can be adjusted to correct for this. In FIG. 11, note the sensed signals sometimes occur simultaneously with the ATP stimulations. When this occurs, crosstalk can prevent this signal from being measured. Therefore, as previously discussed, sensing from more than one sensing channels can help monitor the tachyarrhythmia during ATP therapy. Therefore, the multiple sensing electrodes can be used in combination (and in conjunction with far-field morphology analyses) to assess for entrainment, conduction delay, and changes in the tachyarrhythmia (such as termination or acceleration). Therefore, in one embodiment, catheters with two or more electrodes are described in order to sense cardiac depolarizations from more than one location in order to avoid sensing issues (blanking), which may occur when otherwise sensing from one location.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A method for delivering therapy using an implant including a processor and a plurality of electrodes implanted in a patient's body adjacent a heart to terminate a ventricular tachycardia event, comprising:
   sensing cardiac signals from the heart via one or more of the plurality of electrodes, the processor coupled to the one or more of the plurality of electrodes to identify a ventricular tachycardia in response to the sensed cardiac signals having a tachycardia cycle length;
   delivering a plurality of overdrive pacing pulses to the heart via one or more pacing electrodes, the overdrive pacing pulses having overdrive pacing cycle lengths sufficient to advance or terminate the tachycardia;
   monitoring cardiac signals via one or more sensing electrodes spaced apart from the one or more pacing electrodes and the processor while delivering the overdrive pacing pulses to identify local depolarization of the heart after each overdrive pacing pulse;
   measuring time intervals between a time that the overdrive pacing pulses are transmitted by the one or more pacing electrodes and a time at which subsequent local depolarizations are identified by the one or more sensing electrodes; and
   adjusting delivery of the overdrive pacing pulses based at least in part on the time intervals between the overdrive pacing pulses and subsequent local depolarizations.

2. The method of claim 1, wherein monitoring cardiac signals comprises a combination of monitoring the cardiac signals using the one or more sensing electrodes and far-field morphology analyses.

3. The method of claim 2, further comprising the processor recording one or more time intervals from the one or more pacing electrodes to the one or more sensing electrodes when not in a ventricular tachycardia to assist in monitoring the ventricular tachycardia.

4. The method of claim 3, wherein if the measured time intervals indicate there has been conduction block within the ventricular tachycardia, adjusting delivery comprises stopping delivery of the overdrive pacing pulses.

5. The method of claim 1, wherein adjusting delivery of the overdrive pacing pulses comprises continuing to deliver overdrive pacing pulses at the overdrive pacing cycle lengths until the measured time intervals are unchanged for two consecutive pulses within a specified threshold.

6. The method of claim 5, wherein adjusting delivery of the pacing pulses includes delivering one or more priming pulses via the one or more pacing electrodes, the priming pulses having priming pulse lengths longer than the overdrive pacing cycle lengths used to advance the tachycardia via the one or more pacing electrodes; and
   thereafter, delivering at least one accelerating pulse via the one or more pacing electrodes, the at least one accelerating pulse having an accelerating pulse length shorter than the priming pulse lengths.

7. The method of claim 6, wherein the priming pulse cycle lengths are determined based at least in part on the measured time intervals and the tachycardia cycle length.

8. The method of claim 6, wherein adjusting delivery of the pacing pulses further comprises, when the processor has not confirmed that the tachycardia has terminated after delivering the at least one accelerating pulse, alternating between delivery of at least one priming pulse having a priming pulse length longer than the pacing cycle lengths followed by at least one accelerating pulse having an accelerating pulse length shorter than the priming pulse length.

9. The method of claim 1, wherein the ventricular tachycardia has a tachycardia cycle length (TCL), and wherein the overdrive pacing cycle lengths (PCL) are shorter than the tachycardia cycle length (PCL<TCL).

10. The method of claim 1, wherein:
    delivering a plurality of pacing pulses comprises delivering a first set of one or more pacing pulses to the heart via the one or more pacing electrodes, the one or more pacing pulses having pacing cycle lengths sufficient to advance, entrain, or terminate the tachycardia; and
    adjusting delivery of the pacing pulses comprises:
       after delivering the first set of one or more pacing pulses, delivering a second set of one or more priming pulses with priming pulse intervals longer than the pacing cycle lengths via the one or more pacing electrodes; and
       thereafter, delivering at least one accelerating pulse with an accelerating pulse interval shorter than the priming pulse intervals.

11. The method of claim 1, wherein adjusting delivery of the pacing pulses comprises:
    identifying, by the processor, that the tachycardia has been terminated based on a most recent of the time intervals; and
    thereafter, stopping delivery of the pacing pulses.

12. A system for delivering therapy to terminate a tachycardia event in a heart of a patient, comprising:
    a pacing device configured to be implanted in the patient's body and comprising a processor;
    a plurality of electrodes coupled to the processor and sized for implantation within the patient's body;
    wherein the processor is configured to:
    sense cardiac signals from the heart via one or more electrodes of the plurality of electrodes and detect a ventricular tachycardia in response to the sensed cardiac signals having a tachycardia cycle length;
    deliver a plurality of overdrive pacing pulses to the heart via one or more pacing electrodes, the overdrive pacing pulses having overdrive pacing cycle lengths sufficient to advance or terminate the tachycardia;
    monitor cardiac signals via one or more sensing electrodes spaced apart from the pacing electrodes while delivering the overdrive pacing pulses to identify local depolarization of the heart after each overdrive pacing pulse by the one or more sensing electrodes;
    measure time intervals between a time that the overdrive pacing pulses are transmitted by the one or more pacing electrodes and a time at which subsequent local depolarizations are identified by the one or more sensing electrodes; and
    adjust delivery of the overdrive pacing pulses based at least in part on the time intervals between the overdrive pacing pulses and subsequent local depolarizations.

13. The system of claim 12, wherein the processor is further configured to monitor the cardiac signals using a combination of monitoring the cardiac signals using the one or more sensing electrodes and far-field morphology analyses.

14. The system of claim 13, wherein the processor is further configured to record one or more time intervals from the one or more pacing electrodes to the one or more sensing electrodes when not in a ventricular tachycardia to assist in monitoring the ventricular tachycardia.

15. The system of claim 11, wherein the processor is further configured to continue to deliver overdrive pacing pulses at the overdrive pacing cycle lengths until the measured time intervals are unchanged for two consecutive pulses within a specified threshold.

16. The system of claim 15, wherein the processor is further configured to adjust delivery of the pacing pulses to include delivering one or more priming pulses via the one or more pacing electrodes, the priming pulses having priming pulse lengths longer than the overdrive pacing cycle lengths used to advance the tachycardia via the one or more pacing electrodes, and, thereafter, delivering at least one accelerating pulse via the one or more pacing electrodes, the at least one accelerating pulse having an accelerating pulse length shorter than the priming pulse lengths.

17. The system of claim 16, wherein the processor is further configured to determine the priming pulse cycle lengths based at least in part on the measured time intervals and the tachycardia cycle length.

18. The system of claim 7, wherein the processor is further configured such that, when the processor has not confirmed that the tachycardia has terminated after delivering the at least one accelerating pulse, the processor alternates between delivery of at least one priming pulse having a priming pulse length longer than the pacing cycle lengths followed by at least one accelerating pulse having an accelerating pulse length shorter than the priming pulse length.

* * * * *